United States Patent
Lu et al.

(10) Patent No.: US 12,257,214 B2
(45) Date of Patent: Mar. 25, 2025

(54) COMPOSITIONS AND METHODS COMPRISING DEOXY-PENTITOLS

(71) Applicant: The Charlotte Mecklenburg Hospital Authority, Charlotte, NC (US)

(72) Inventors: Qi Long Lu, Charlotte, NC (US); Pei Juan Lu, Charlotte, NC (US)

(73) Assignee: The Charlotte Mecklenburg Hospital Authority, Charlotte, NC (US)

(*) Notice: Subject to any disclaimer, the term of this patent is extended or adjusted under 35 U.S.C. 154(b) by 84 days.

(21) Appl. No.: 17/830,858

(22) Filed: Jun. 2, 2022

(65) Prior Publication Data

US 2022/0387346 A1    Dec. 8, 2022

Related U.S. Application Data

(60) Provisional application No. 63/195,897, filed on Jun. 2, 2021.

(51) Int. Cl.
| | | |
|---|---|---|
| *A61K 31/047* | (2006.01) | |
| *A61K 45/06* | (2006.01) | |
| *A61P 35/00* | (2006.01) | |

(52) U.S. Cl.
CPC ............ *A61K 31/047* (2013.01); *A61K 45/06* (2013.01); *A61P 35/00* (2018.01)

(58) Field of Classification Search
CPC .................................................. A61K 31/047
See application file for complete search history.

(56) References Cited

U.S. PATENT DOCUMENTS

| | | | | |
|---|---|---|---|---|
| 8,697,659 B2 * | 4/2014 | Panza | ...................... | A61P 31/12 |
| | | | | 514/25 |
| 11,931,371 B2 * | 3/2024 | Lu | ....................... | A61K 31/047 |
| 2014/0121175 A1 | 5/2014 | Sugiura et al. | | |
| 2014/0134193 A1 * | 5/2014 | Subramanyam | ..... | A61K 31/496 |
| | | | | 548/953 |
| 2016/0022620 A1 | 1/2016 | Suovaniemi | | |
| 2017/0189425 A1 | 7/2017 | Bannister et al. | | |
| 2022/0016145 A1 * | 1/2022 | Lu | ........................ | A61K 31/047 |

OTHER PUBLICATIONS

Saha et. al.(Translational Research, vol. 165, Issue 5, May 2015, pp. 558-577) (Year: 2015).*
Kaminski et.al (The Journal of Biological Chemistry vol. 285, No. 53, pp. 41806-41814, Dec. 31, 2010) (Year: 2010).*
Schimmel et. al (Archives of Biochemistry and Biophysics 164, 560-570, 1974) (Year: 1974).*
Lu et al. "Ribitol enhances matriglycan of alpha-dystroglycan in breast cancer cells without affecting cell growth" Scientific Reports, 10:4935 (2020).
Rosenberg, Steven A. "The immunotherapy of solid cancers based on cloning the genes encoding tumor-rejection antigens" Annual Review of Medicine, 47:481-491 (1996).
Tyle, Praveen "Iontophoretic Devices for Drug Delivery" Pharmaceutical Research, 3:318-326 (1986).
"International Preliminary Report on Patentability corresponding to International Patent Application No. PCT/US2022/031867 mailed Dec. 14, 2023".
International Search Report and the Written Opinion of the International Searching Authority corresponding to International Patent Application No. PCT/US2022/31867 (10 pages) (mailed Aug. 18, 2022).

* cited by examiner

*Primary Examiner* — John S Kenyon
*Assistant Examiner* — Rehana Ismail
(74) *Attorney, Agent, or Firm* — Myers Bigel, P.A.

(57) ABSTRACT

The present invention is related to pharmaceutical formulations comprising a synthetic deoxypentitol and methods of use thereof in treating cancer.

20 Claims, 8 Drawing Sheets

Deoxy at different carbon

2-deoxyribitol  3-deoxyribitol  4-deoxyribitol

Modified 2 carbon position

2-fluoro-2-deoxy-d-ribitol (2DFR),  2-bromo-2-deoxy-d-ribitol (2DBR)  2-chloro-2-deoxy-d-ribitol (2DCR)

Other modifications or epimers

3, or 5, or 3 and 5 acetyl-deoxyribitol  2-deoxyxylitol (Epimer of 2-deoxyribitol)

COMPOSITIONS AND METHODS COMPRISING DEOXY-PENTITOLS

PRIORITY STATEMENT

This application claims the benefit, under 35 U.S.C. § 119(e), of U.S. Provisional Application Ser. No. 63/195,897, filed Jun. 2, 2021, the entire contents of which are incorporated by reference herein.

FIELD OF THE INVENTION

The present invention is related to pharmaceutical formulations comprising a synthetic deoxypentitol and methods of use thereof in treating cancer.

BACKGROUND OF THE INVENTION

Cancer is one of the leading causes of death for all age groups around the world. Cancer incidence reaches more than 0.4% of population and death rate of 0.2% of population each year. Despite decades of tremendous effort to cure cancer, most solid tissue cancers, including most common breast, liver, and prostate cancers remain incurable unless the tumors are discovered at very early stage with complete excision. Currently, surgical removal, radiation therapy and chemotherapy remain the principal approaches to treat solid tissue cancers. However, surgery is limited to those tumors located locally, while radiation therapy also can only be applied to limited type of sensitive cancers in limited areas, often with severe side effects. Chemotherapy often indiscriminately kills normal cells as well as cancer cells, and thus has high toxicity and limited long-term effect. More recently, targeted immune therapy has also been tested, but its efficacy is limited in degree and in patient population.

It remains a challenge to develop effective treatment to most solid tissue cancers, especially in their later stage.

SUMMARY OF THE INVENTION

One aspect of the present invention provides a method of treating cancer in a subject in need thereof, comprising administering to the subject an effective amount of a composition comprising a synthetic deoxypentitol, thereby treating the cancer in the subject.

An additional aspect of the present invention provides a method of inhibiting and/or reducing metastasis of cancer cells in a subject in need thereof, comprising administering to the subject an effective amount of a composition comprising a synthetic deoxypentitol, thereby inhibiting and/or reducing metastasis of the cancer cells in the subject.

A further aspect of the present invention provides a method of inducing cell death of cancer cells in a subject in need thereof, comprising administering to the subject an effective amount of a composition comprising a synthetic deoxypentitol.

In some embodiments, the administration of the synthetic deoxypentitol may be in combination with any other anticancer treatment.

Another aspect of the present invention provides a method of enhancing the therapeutic efficacy of an anticancer agent in a subject having or at risk of cancer and receiving said anticancer agent, comprising administering to the subject an effective amount of a composition comprising a synthetic deoxypentitol, thereby enhancing the therapeutic efficacy of the anticancer agent in the subject.

BRIEF DESCRIPTION OF THE DRAWINGS

FIG. 3 top left panel shows Control, without Drug treatment, and with 2-deoxyribitol treatment of 10 mM (top middle panel) and 20 mM (top right panel) concentration. FIG. 3 lower left panel shows a bar graph quantifying the number of colonies counted per field of ×100 magnification. Stars indicate a significant difference as compared to the control ($p<0.01$, $n=3$). FIG. 3 lower middle panel shows an image of cell colonies grown out in the culture without Drug treatment (Control). FIG. 3 lower right panel shows an image of the absence of cell colony in the culture treated with 10 mM 2-deoxyribitol.

Figure 9:
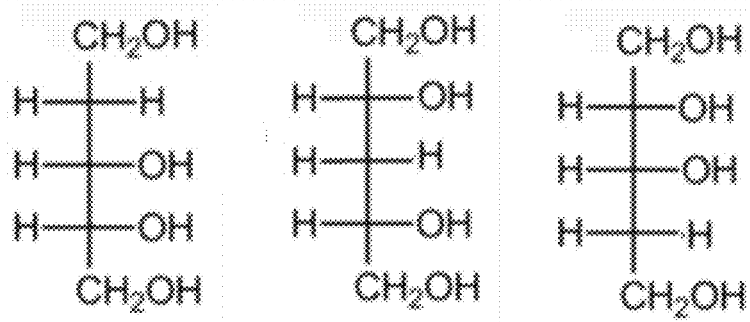
Figure 9:
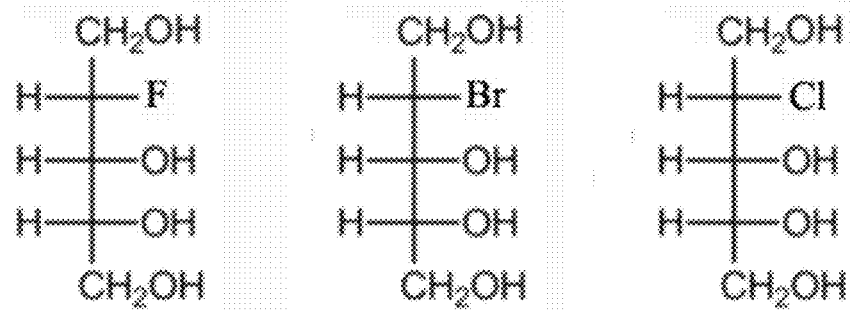
Figure 9:
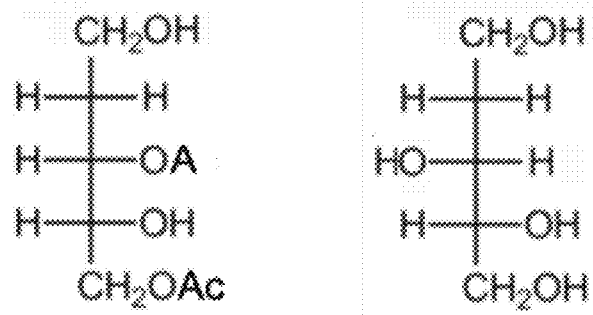

FIG. 9 shows structures of other nonlimiting examples of synthetic deoxypentitols of the invention.

Figure 10:
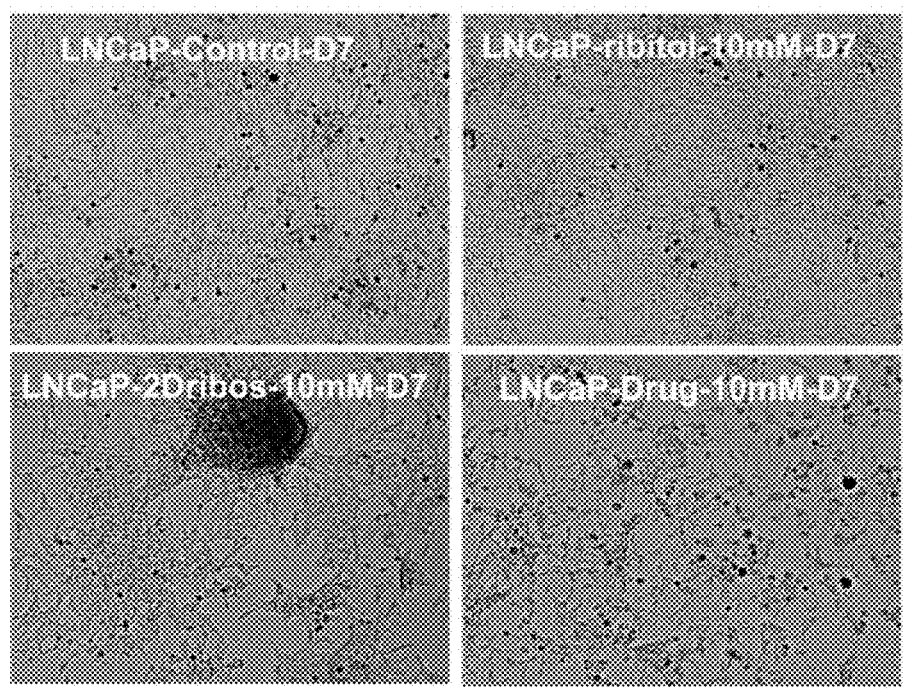

FIG. 10 shows microscopy images of prostate cancer cell LNCaP treated with 10 mM ribitol (top right) 10 mM 2-deoxyribose (2Dribos; bottom left) and 10 mM 2-deoxyribitol (Drug; bottom right) for 7 days. Only 2-deoxyribitol treatment markedly reduces the number of cancer cells.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations, and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A. B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "modulate," "modulates." or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

The term "contact" or grammatical variations thereof as used with respect to a polypeptide and a calcium channel, refers to bringing the polypeptide and the calcium channel in sufficiently close proximity to each other for one to exert a biological effect on the other. In some embodiments, the term contact means binding of the polypeptide to the calcium channel.

By the terms "treat," "treating," or "treatment of," it is intended that the severity of the subject's condition is reduced or at least partially improved or modified and that some alleviation, mitigation or decrease in at least one clinical symptom is achieved. "Subject" as used herein includes any animal in which treatment with a synthetic deoxypentitol is necessary or desired. In some embodiments, the subject is any animal that can receive a beneficial and/or therapeutic effect from administration of a synthetic deoxypentitol of the present invention. Suitable subjects include, but not are limited to, mammals. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a composition including those described herein. For example, in particular embodiments, the subject has (or has had) or is at risk for a cancer. As a further option, the subject can be a laboratory animal and/or an animal model of disease. In some embodiments, the subject is a mammal and in particular embodiments, the subject is a human of any age, race, gender, or ethnicity, etc. In some embodiments, the subject may be a human patient.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "therapeutically effective" or "effective" amount as used herein is an amount that provides some improvement or benefit to the subject. Alternatively stated, a "therapeutically effective" amount or an "effective amount" is an amount that will provide some alleviation, mitigation, or decrease in at least one clinical symptom in the subject. Those skilled in the art will appreciate that the effects need not be complete or curative, as long as some benefit is provided to the subject.

A "prophylactically effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. These terms are intended to be relative to a reference or control.

The above terms are relative to a reference or control. For example, in a method of enhancing the therapeutic efficacy of an anticancer agent in a subject of this invention by administering a synthetic deoxypentitol of the invention to the subject, the enhancement is relative to the efficacy of the anticancer agent in a subject (e.g., a control subject) in the absence of administration of the synthetic deoxypentitol.

As used herein, the term "synthetic" (e.g., synthetic deoxypentitol) refers to an agent (e.g., a molecule and/or a compound) generated non-naturally (e.g., synthesized) by deliberate human design. Structural and functional components of the synthetic molecule or compound may be incorporated from differing and/or a plurality of source material. The synthetic product may be delivered exogenously to a subject, wherein it would be exogenous in comparison to any corresponding endogenous product.

"Isolated" as used herein means the synthetic deoxypentitol of this invention is sufficiently free of contaminants or cell components with which starting compounds may occur. "Isolated" does not mean that the preparation is technically pure (homogeneous), but it is sufficiently pure to provide the synthetic deoxypentitol in a form in which it can be used therapeutically.

The term "prevent," "preventing" or "prevention of" (and grammatical variations thereof) refers to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the at will appreciate that the level of prevention need not be complete, as long as some benefit is provided to the subject.

"Concurrently administering" or "concurrently administer" as used herein means that the two or more compounds or compositions are administered closely enough in time to produce a combined effect (that is, concurrently may be simultaneously, or it may be two or more events occurring within a short time period before and/or after each other, e.g., sequentially). Simultaneous concurrent administration may be carried out by mixing the compounds prior to administration, or by administering the compounds at the same point in time but at different anatomic sites and/or by using different routes of administration.

"Pharmaceutically acceptable" as used herein means that the compound or composition is suitable for administration to a subject to achieve the treatments described herein, without unduly deleterious side effects in light of the severity of the disease and necessity of the treatment.

Compositions Comprising a Synthetic Deoxypentitol and Methods of Use.

The present invention relates, in part, to compositions and methods of using a synthetic deoxypentitol in the treatment of diseases such as cancers.

It remains a challenge to develop effective treatment to most solid tissue cancers, especially in their later stage. Cancer cells have characteristic metabolic features, including aerobic glycolysis (Warburg effect) to meet the demand for their growth and invasion and alteration of metabolic pathways is considered to have high potential for cancer treatment. However, no metabolite has been demonstrated to have sufficient effect on cancer growth and invasion. The inventors of the present invention have found that 2-deoxyribitol can effectively inhibit cancer cell growth and tumorigenicity alone, and can enhance anti-cancer effects of other anticancer treatments, such as, but not limited to, chemotherapeutics and/or immunotherapeutics, in cancers such as in breast, prostate and liver cancers. While not wishing to be bound by theory, the inventors of the present application found 2-deoxyribitol to show extremely limited to no toxicity to non-cancer cells and to normal muscle cells. These characteristics may provide wide applications to treat many cancers, including those at later stages of disease and/or resistant to chemotherapy and/or other anticancer treatments.

While not wishing to be bound to theory, the inventors of the present invention theorized that the chemical structure of 2-deoxyribitol may be amenable to chemical modifications at sites other than the carbon 2 position, and/or modifications other than reduction, and also achieve anticancer effect. For example, such further chemical modifications and formulations of 2-deoxyribitol may improve delivery for higher efficacy. Additional nonlimiting examples of synthetic deoxypentitols of the invention are shown in FIG. 9. Other synthetic molecules may be generated, for example, via modifications including having the deoxy-group at one or more different carbons of the synthetic deoxypentitol; via modifications of the 2-carbon position, which may enhance target selectivity and/or effectivity of the molecule; via acetylation at one or more other carbon sites other than the deoxy-group, which may enhance delivery of the molecule; and/or via epimerization of any of the synthetic deoxypentitols of the invention.

Thus, one aspect of the present invention provides a method of treating cancer in a subject in need thereof, comprising administering to the subject an effective amount of a composition comprising a synthetic deoxypentitol, thereby treating the cancer in the subject.

Another aspect of the present invention provides a method of inhibiting and/or reducing metastasis of cancer cells in a subject in need thereof, comprising administering to the subject an effective amount of a composition comprising a synthetic deoxypentitol, thereby inhibiting and/or reducing metastasis of the cancer cells in the subject.

An additional aspect of the present invention provides a method of inducing cell death of cancer cells in a subject in need thereof, comprising administering to the subject an effective amount of a composition comprising a synthetic deoxypentitol.

In some embodiments of the methods of this invention, the synthetic deoxypentitol can be administered or delivered to a subject in combination with (e.g., simultaneously, before and/or after) any other anticancer agent and or anticancer treatment in an amount effective for enhancing the effect of the synthetic pentitol and/or the other anticancer agent and/or anticancer treatment. Furthermore, in the methods of this invention, the synthetic deoxypentitol may be administered with any other therapy (simultaneously (e.g., administered simultaneously in separate formulations and/or in combination in a single formulation), before and/or after), such as an immunotherapeutic, radiotherapeutic, and/or chemotherapeutic to enhance or increase the therapeutic effect.

Nonlimiting examples of a cancer that can be treated according to the methods of this invention include lymphoma (e.g., Hodgkin and non-Hodgkin lymphomas, B cell lymphoma, T cell lymphoma, and the like), myeloma, leukemia, hematopoietic neoplasias, thymoma, sarcoma, lung cancer, liver cancer, uterine cancer, cervical cancer, endometrial cancer, adenocarcinoma, breast cancer, pancreatic cancer, colon cancer, anal cancer, lung cancer, renal cancer, bladder cancer, liver cancer, prostate cancer, ovarian cancer, primary or metastatic melanoma, squamous cell carcinoma, basal cell carcinoma, brain cancer (e.g., gliomas and glioblastoma), angiosarcoma, hemangiosarcoma, head and neck carcinoma, thyroid carcinoma, soft tissue sarcoma, bone sarcoma, gastrointestinal cancer, colorectal cancer, esophageal cancer, thyroid cancer, and the like. Additional exemplary cancers treatable by the compositions and methods of the invention include, but are not limited to, biliary tract cancer; choriocarcinoma; endometrial cancer; hematological neoplasms, including acute lymphocytic and myelogenous leukemia; multiple myeloma; AIDS associated leukemias and adult T-cell leukemia lymphoma; neuroblastomas; oral cancer, including squamous cell carcinoma; ovarian cancer, including those arising from epithelial cells, stromal cells, germ cells and mesenchymal cells; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; renal cancer including adenocarcinoma and Wilms tumor; those cancers listed in Table 1, Table 2, and Table 3, and any other cancer now known or later identified (see, e.g., Rosenberg (1996) Ann. Rev. Med. 47:481-491, the entire contents of which are incorporated by reference herein).

The term "tumor" is understood in the art, for example, as an abnormal mass of undifferentiated cells within a multicellular organism. Tumors can be malignant or benign. In representative embodiments, the methods disclosed herein are used to prevent and treat malignant tumors.

The term "cancer" has its understood meaning in the art, for example, an uncontrolled growth of tissue that has the potential to spread to distant sites of the body (i.e., metastasize). As used herein, the term "cancer" encompasses all malignant tumors, e.g., capable of invading and metastasizing to normal tissues. Likewise, the term "cancerous tissue" encompasses malignant tumors. A "cancer cell antigen" encompasses tumor antigens.

By the terms "treating cancer" or "treatment of cancer," it is intended that the severity of the cancer is reduced or the cancer is prevented or at least partially eliminated. For example, in particular contexts, these terms indicate that metastasis of the cancer is prevented or reduced or at least partially eliminated. In further representative embodiments these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset or progression of cancer in the subject may be slowed, controlled, decreased in likelihood or probability, or delayed.

In some embodiments, the cancer may be a malignant tumor. In some embodiments, the cancer may be a blood cancer and/or a solid tissue cancer. In some embodiments, the cancer may be leukemia. In some embodiments, the cancer may be breast cancer (including, but not limited, to triple-negative breast cancer), liver cancer, prostate cancer, or any combination thereof.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (e.g., CTL inductive cytokines) may be administered to a subject in conjunction with the synthetic deoxypentitol.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

In some embodiments, the anticancer agent may be one or more antibody (e.g., an anticancer antibody). In some embodiments, the antibody may be selected from Table 1. The antibody may be a biosimilar version thereof. Biosimilars of antibodies in Table 1 include, but are not limited to, bevacizmab-awwb ("Mvasi") as a biosimilar of bevacizumab, GP2013 and rituximab-abbs ("Truxima") as biosimilars of rituximab, trastuzumab-dkst ("Ogivri"), trastuzumab-dttb ("Ontruzant"), and trastuzumab-pkrb ("Herzuma") as biosimilars of trastuzumab.

In some embodiments, the anticancer agent may be one or more chemotherapeutic agent(s) such as, but not limited to, abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, cyclophosphamide, bendamustine, bortezomib, cabazitaxel, chlorambucil, dasatinib, docetaxel, doxorubicin, epirubicin, erlotinib, idarubicin, hydroxyurea, imatinib, adriamycin, prednisone, dexamethasone, cytarabine, thiotepa, ifosfamide, dacarbazine, bleomycin, ibrutinib, campath-B, gemcitabine, revlimid, sirolimus, temsirolimus, bexxar, brentuximab, bendamustine, vedotin, emtansine, and/or those listed in Table 2.

In some embodiments, the anticancer agent may be an agent with anticancer benefits, such as agent(s) which may enhance non-cancer cell survival, including, but not limited to, agents targeting cell survival related genes such as Bcl-xL, Bcl-2, and/or Mcl-1. In some embodiments, the anticancer agent may be an agent with anticancer benefits, such as agent(s) which may inhibit cancer cell survival, including, but not limited to, cancer-targeted (cancer antigen-targeted) inhibitory agents targeting cell survival related genes such as Bcl-xL, Bcl-2, and/or Mcl-1.

As another example, in some embodiments, a composition of the present invention may be administered with (before, concurrently with, and/or after) other treatment for cancer, such as with radiation therapy of any kind; with surgical excision of cancer tissue; with a bone allograft, for example, following a break or surgical removal in a cancer patient; and/or any other non-drug anticancer treatment.

Additional illustrative anticancer agents and/or treatments include, but are not limited to: endostatin, angiostatin, TRAIL, FAS-ligand, cytokines including interferons; inhibitory RNA including without limitation RNAi (such as siRNA or shRNA), antisense RNA and microRNA including inhibitory RNA against VEGF, the multiple drug resistance gene product or a cancer immunogen, astrocytomas [endostatin, angiostatin and/or RNAi against VEGF], glioblastomas [endostatin, angiostatin and/or RNAi against VEGF]), doxorubicin, cyclophosphamide, 5-flurouracil, vinorelbine, pembrolizumab, nivolumab, durvalumab, paclitaxel, docetaxel, oligomycin, JQ1, emodin, metformin, shikonin, physcion (6PGD inhibitor), AICAR, oxythiamine, leflunomide, lonidamine, polydatin, honokiol, dehydropiandrosterone (DHEA), venetoclax (ABT-199, Bcl-2 inhibitor), navitoclax (ABT-263), A-1331852 (Bcl-xL inhibitor), ABT-737, S63845 (Mcl-1 inhibitor) and any combination thereof.

An additional aspect of the present invention provides a method of enhancing the therapeutic efficacy of an anticancer agent in a subject having or at risk of cancer and receiving said anticancer agent, comprising administering to the subject an effective amount of a composition comprising a synthetic deoxypentitol, thereby enhancing the therapeutic efficacy of the anticancer agent in the subject.

In some embodiments, the enhanced therapeutic efficacy of an anticancer agent may be combinatorial with that of a synthetic deoxypentitol of the present invention (e.g., additive). In some embodiments, the enhanced therapeutic efficacy of an anticancer agent may be synergistic with that of a synthetic deoxypentitol of the present invention (e.g., more than the sum of the individual therapeutic efficacies of each treatment alone).

In some embodiments, the administration of the synthetic deoxypentitol may be before, after, and/or concurrent with the administration of the anticancer agent or any other cancer treatment.

As used herein, the term "synthetic deoxypentitol" of the present invention comprises any deoxypentitol (i.e., any deoxy sugar alcohol having five carbons) of any position and/or with any additional modification and/or substituent. For example, in some embodiments, the synthetic deoxypentitol of the present invention may be, but is not limited to, 2-deoxyribitol, 3-deoxyribitol, 4-deoxyribitol, 2-fluoro-2-deoxy-d-ribitol (2DFR), 2-amino-2-deoxy-d-ribitol, 3-amino-2-deoxy-d-ribitol, 2-bromo-2-deoxy-d-ribitol (2DBR), 2-chloro-2-deoxy-d-ribitol (2DCR), 3-acetyldeoxyribitol, 5-acetyldeoxyribitol, 3,5-acetyldeoxyribitol), any epimer thereof (e.g., 2-deoxyxylitol), and any combination thereof. In some embodiments, the synthetic deoxypentitol of the present invention may be a deoxyribitol, e.g., 2-deoxyribitol, 3-deoxyribitol, and/or 4-deoxyribitol.

In some embodiments, the administration of the synthetic deoxypentitol may inhibit growth of cancer stem cells, such as, but not limited to, mammospheres in breast cancer and the like.

In some embodiments, the administration of the synthetic deoxypentitol of the present invention may have reduced toxicity to non-cancer cells as compared to cancer cells. For example, in some embodiments, the administration of the synthetic deoxypentitol may have a reduced toxicity of less than 50, 45, 40, 35, 30, 25, 20, 15, 10, 9, 8.7, 6, 5, 4, 4, 3, 2, or 1% toxicity to non-cancer cells as compared to cancer cells. In some embodiments, reduced toxicity of a deoxypentitol of the present invention may comprise reduced cell death induction in non-cancer cells as compared to cancer cells. In some embodiments, the administration of the synthetic deoxypentitol of the present invention may not have reduced toxicity to non-cancer cells as compared to cancer cells, e.g., may have the same toxicity to non-cancer cells as compared to cancer cells.

In some embodiments, administering the synthetic deoxypentitol of the present invention may have no effect on the levels of glycosylated alpha-dystroglycan ($\alpha$-DG), e.g., does not enhance levels of $\alpha$-DG and/or does not enhance glycosylation of cellular proteins (e.g., as compared to glycosylation thereof without administering the synthetic deoxypentitol).

Administration of a compound or composition comprising the synthetic deoxypentitol of this invention may be by any suitable route, including, but not limited to, topically (e.g., direct application), intravenously, cutaneously, subcutaneously, intraperitoneally, intra-arterially, intratumorally, intrathecally, intramuscularly, orally (e.g., by oral tablet or capsule), intranasally, sublingually, via inhalation, in an implant, in a matrix, in a gel, or any combination thereof.

Determination of a therapeutically effective and/or prophylactically effective amount, as well as other factors related to effective administration of a compound of the present invention to a subject of this invention, including dosage forms, routes of administration, and frequency of dosing, may depend upon the particulars of the condition that is encountered, including the subject and condition being treated or addressed, the severity of the condition in a particular subject, the particular compound being employed, the particular route of administration being employed, the frequency of dosing, and the particular formulation being employed. Determination of a therapeutically effective and/or prophylactically effective treatment regimen for a subject of this invention is within the level of ordinary skill in the medical or veterinarian arts. In clinical use, an effective amount may be the amount that is recommended by the U.S. Food and Dug Administration, or an equivalent foreign agency. The amount of active ingredient that can be combined with the carrier materials to produce a single dosage form varies depending upon the subject being treated and the particular mode of administration.

In some embodiments, the therapeutically effective amount of the synthetic deoxypentitol is between about 1 µM to about 50 mM. e.g., about 1 µM, 10 µM, 20 µM, 30 µM, 40 µM, 50 µM, 60 µM, 70 µM, 80 µM, 90 µM, 100 µM, 125 µM, 150 µM, 175 µM, 200 µM, 250 µM, 300 µM, 350 µM, 400 µM, 450 µM, 500 µM, 550 µM, 600 µM, 650 µM, 700 µM, 750 µM, 800 µM, 850 µM, 900 µM, 950 µM, 1000 µM (1 mM), 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 nM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, or 50 mM, or any value or range therein. For example, in some embodiments, a therapeutically effective amount of the synthetic deoxypentitol of the present invention may be about 50 µM to about 10 mM, about 100 µM to about 15 mM, about 250 µM to about 20 mM, about 0.5 mM to about 10 mM, or about 50 µM, about 100 µM, about 500 µM (0.5 mM), about 5 mM, about 10 mM, or about 50 mM.

Further aspects of this invention include the use of a synthetic deoxypentitol and/or a composition of this invention in the preparation of a medicament for carrying out the methods of this invention.

An additional aspect is the use of a synthetic deoxypentitol and/or a composition of this invention for carrying out the methods of this invention.

Accordingly, in some embodiments, the composition comprising the synthetic deoxypentitol of the invention may further comprise a pharmaceutically acceptable carrier (e.g., a pharmaceutical formulation).

The active compound of this invention (e.g., the synthetic deoxypentitol, e.g., 2-deoxyribitol, 3-deoxyribitol, 4-deoxyribitol, 2-fluoro-2-deoxy-d-ribitol (2DFR), 2-amino-2-deoxy-d-ribitol, 3-amino-2-deoxy-d-ribitol, 2-bromo-2-deoxy-d-ribitol (2DBR), 2-chloro-2-deoxy-d-ribitol (2DCR), 3-acetyldeoxyribitol, 5-acetyldeoxyribitol, 3,5-acetyldeoxyribitol), any epimer thereof (e.g., 2-deoxyxylitol), and any combination thereof) may be present in a pharmaceutical formulation that comprises substances and/or agents that are not natural products. As a nonlimiting example, the active compound (e.g., the synthetic deoxypentitol, e.g., 2-deoxyribitol, 3-deoxyribitol, 4-deoxyribitol, 2-fluoro-2-deoxy-d-ribitol (2DFR), 2-amino-2-deoxy-d-ribitol, 3-amino-2-deoxy-d-ribitol, 2-bromo-2-deoxy-d-ribitol (2DBR), 2-chloro-2-deoxy-d-ribitol (2DCR), 3-acetyldeoxyribitol, 5-acetyldeoxyribitol, 3,5-acetyldeoxyribitol), any epimer thereof (e.g., 2-deoxyxylitol), and any combination thereof) of this invention can be present in a pharmaceutical composition with polyethylene glycol (PEG), which in some embodiments can have a molecular weight (MW) in a range of about 200 to about 500. In some embodiments, a pharmaceutical composition of this invention can comprise glucose.

In some embodiments, the active compound of this invention (e.g., the synthetic deoxypentitol, e.g., 2-deoxyribitol, 3-deoxyribitol, 4-deoxyribitol, 2-fluoro-2-deoxy-d-ribitol (2DFR), 2-amino-2-deoxy-d-ribitol, 3-amino-2-deoxy-d-ribitol, 2-bromo-2-deoxy-d-ribitol (2DBR), 2-chloro-2-deoxy-d-ribitol (2DCR), 3-acetyldeoxyribitol, 5-acetyldeoxyribitol, 3,5-acetyldeoxyribitol), any epimer thereof (e.g., 2-deoxyxylitol), and any combination thereof) can comprise a polyalkylene glycol moiety coupled or linked thereto. "Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol (PAG) of the composition is polyethylene glycol or "PEG." The term "PEG subunit" refers to a single polyethylene glycol unit, i.e., $-(CH_2CH_2O)-$. Thus, the active compound can be "pegylated." In some embodiments, the PEG can have a molecular weight from about 10,000 g/mol to about 30,000 g/mol.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

Pharmaceutical Formulations.

The active compounds described herein may be formulated for administration in a pharmaceutical carrier in accordance with known techniques. See, e.g., Remington, The Science and Practice of Pharmacy (21st Ed. 2005). In the manufacture of a pharmaceutical formulation according to the invention, the active compound is typically admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

Furthermore, a "pharmaceutically acceptable" component such as a sugar, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as saline solutions, water, emulsions such as oil/water emulsion, microemulsions and various types of wetting agents.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound, as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., (1986) *Pharmaceutical Research* 3(6):318) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension. Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In some embodiments of this invention, the compound of this invention is present in an aqueous solution for subcutaneous administration. In some embodiments, the compound is provided as a lyophilized powder that is reconstituted and administered subcutaneously.

In some embodiments, the present invention may be as defined in any one of the following numbered paragraphs.

1. A method of treating cancer in a subject in need thereof, comprising administering to the subject an effective amount of a composition comprising a synthetic deoxypentitol, thereby treating the cancer in the subject.
2. A method of inhibiting and/or reducing metastasis of cancer cells in a subject in need thereof, comprising administering to the subject an effective amount of a composition comprising a synthetic deoxypentitol, thereby inhibiting and/or reducing metastasis of the cancer cells in the subject.
3. A method of inducing cell death of cancer cells in a subject in need thereof, comprising administering to the subject an effective amount of a composition comprising a synthetic deoxypentitol.
4. The method of any one of paragraphs 1-3, wherein the administration of the synthetic deoxypentitol is in combination with any other anticancer treatment.
5. A method of enhancing the therapeutic efficacy of an anticancer agent in a subject having or at risk of cancer and receiving said anticancer agent, comprising administering to the subject an effective amount of a composition comprising a synthetic deoxypentitol, thereby enhancing the therapeutic efficacy of the anticancer agent in the subject.
6. The method of paragraph 4 or 5, wherein the administration of the synthetic deoxypentitol is before, after, and/or concurrent with the administration of the anticancer agent or any other cancer treatment.
7. The method of any one of paragraphs 1-6, wherein the synthetic deoxypentitol is selected from the group consisting of a deoxyribitol (e.g., 2-deoxyribitol, 3-deoxyribitol, 4-deoxyribitol, 2-fluoro-2-deoxy-d-ribitol (2DFR), 2-amino-2-deoxy-d-ribitol, 3-amino-2-deoxy-d-ribitol, 2-bromo-2-deoxy-d-ribitol (2DBR), 2-chloro-2-deoxy-d-ribitol (2DCR), 3-acetyldeoxyribitol, 5-acetyldeoxyribitol, 3,5-acetyldeoxyribitol), any epimer thereof (e.g., 2-deoxyxylitol), and any combination thereof.
8. The method of paragraph 7, wherein the synthetic deoxypentitol is a deoxyribitol (e.g., 2-deoxyribitol, 3-deoxyribitol, 4-deoxyribitol).
9. The method of paragraph 8, wherein the deoxyribitol is 2-deoxyribitol.
10. The method of any one of paragraphs 1-9, wherein the administration of the synthetic deoxypentitol inhibits growth of cancer stem cells (e.g., mammospheres in breast cancer).
11. The method of any one of paragraphs 1-10, wherein the synthetic deoxypentitol is administered topically (e.g., direct application), intravenously, cutaneously, subcutaneously, intraperitoneally, intra-arterially, intratumorally, intrathecally, intramuscularly, orally (e.g., by oral tablet or capsule), intranasally, sublingually, via inhalation, in an implant, in a matrix, in a gel, or any combination thereof.
12. The method of any one of paragraphs 1-11, wherein the cancer is a malignant tumor.
13. The method of paragraph 12, wherein the malignant tumor is a solid tissue cancer.
14. The method of paragraph 12 or 13, wherein the cancer is breast cancer (including but not limited to triple-negative breast cancer), liver cancer, prostate cancer, any cancer as listed in Tables 1-3, or any combination thereof.
15. The method of any one of paragraphs 1-14, wherein the therapeutically effective amount of the synthetic deoxypentitol is between about 5 µM to about 50 mM.
16. The method of paragraph 15, wherein the therapeutically effective amount of the synthetic deoxypentitol is between about 0.5 mM to about 10 mM.
17. The method of any one of paragraphs 4-16, wherein the chemotherapeutic agent or other cancer treatment comprises a cancer treatment selected from the group consisting of Doxorubicin, cyclophosphamide, 5-flurouracil, vinorelbine, pembrolizumab, nivolumab, durvalumab, Paclitaxel, Docetaxel, Oligomycin, JQ1, emodin, metformin, shikonin, physcion (6PGD inhibitor), AICAR, oxythiamine, leflunomide, lonidamine, polydatin, honokiol, dehydropiandrosterone (DHEA), venetoclax (ABT-199, Bcl-2 inhibitor), navitoclax (ABT-263), A-1331852 (Bcl-xL inhibitor), ABT-737, S63845 (Mcl-1 inhibitor), and any combination thereof.
18. The method of any one of paragraphs 1-17, wherein the subject is a human patient.
19. The method of any one of paragraphs 1-18, wherein the composition comprising the synthetic deoxypentitol further comprises a pharmaceutically acceptable carrier (e.g., a pharmaceutical formulation).

The present invention is illustrated in the following non-limiting examples.

EXAMPLES

Example 1

This invention applies a synthetic molecule, 2-deoxyribitol, to treat cancer for growth inhibition and cancer cell killing. Naturally-occurring ribitol is a metabolite, but its metabolic pathway has not been clearly defined. Recently, ribitol has been identified as a precursor of CDP-ribitol, the substrate used for the synthesis of sugar modification of a membrane protein, alpha dystroglycan (α-DG). The use of ribitol enhances glycosylation of α-DG in some cancer cells including the breast cancer cell of MCF7. The loss or reduced expression of glycosylation of α-DG has been linked to cancer progression and metastasis in breast and other cancers in clinics, and enhanced glycosylation of α-DG may inhibit cancer cell growth and tumorigenicity. This study screened several different pentose and pentitol molecules including ribose, 2-deoxyribose, ribulose, 2-deoxyribitol, xylose, and xylitol to evaluate these sugar molecules for the effects of enhancing glycosylation of α-DG and inhibiting cancer cell growth/tumorigenicity.

Figure 1:
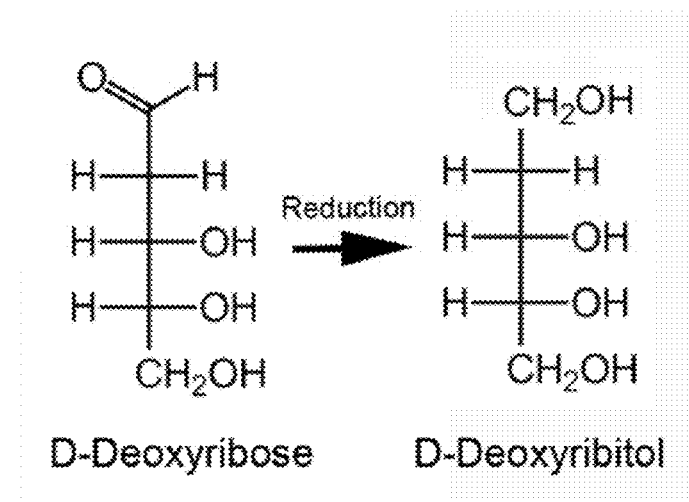
FIG. 1 shows a diagram of 2-deoxyribitol (right) synthesis by reduction from 2-deoxyribose (left).
Figure 2:
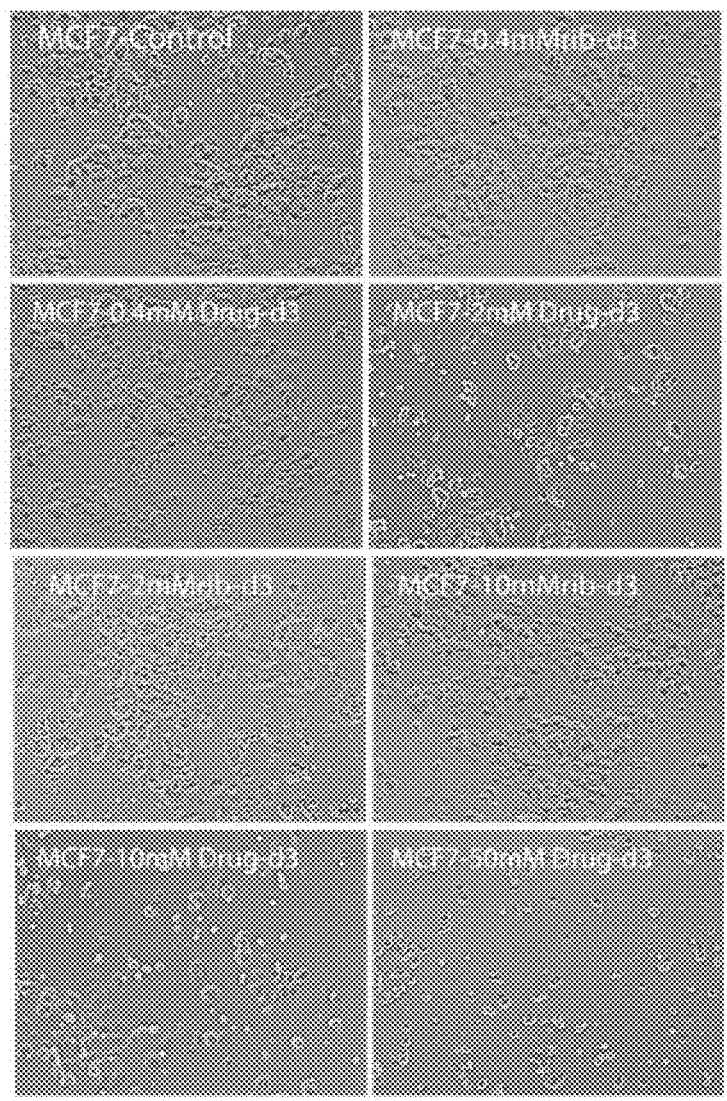
FIG. 2 shows images of MCF7 breast cancer cells cultured in growth medium and treated for 3 day (3d) with 2-deoxyribitol (Drug) or ribitol (rib) at the concentration as stated within the images. From left-top-to-bottom: Control, 0.4 mM Drug, 2 mM rib, and 10 mM Drug; From right-top-to-bottom: 0.4 mM rib; 2 mM Drug; 10 mM rib; and 50 mM Drug.
Figure 3:
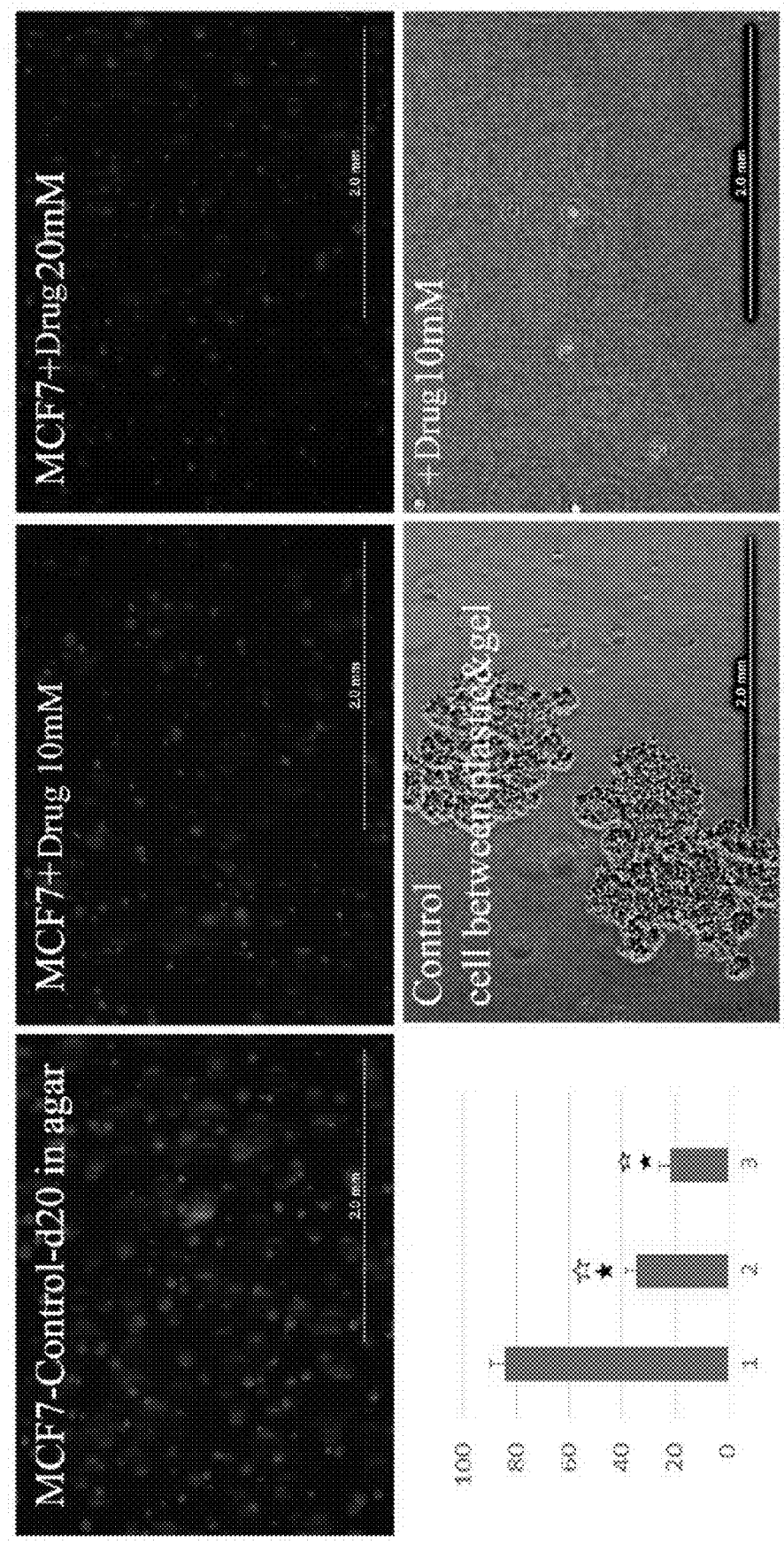
FIG. 3 shows fluorescence microscopy images and a bar graph of MCF7 cells grown in 5% agar for 20 days (d20).

As illustrated in FIG. 1, synthetic 2-deoxyribitol was synthesized by reduction from 2-deoxyribose. Results of cell culture showed surprisingly that only 2-deoxyribitol has the capability to inhibit proliferation of breast cancer cell line MCF7 in the dose range examined. However, this effect was not related to the enhanced expression of glycosylation of α-DG. It was also found that 2-deoxyribitol has a dose-dependent effect on cell growth inhibition and death. As shown in FIG. 2, ribitol had no clear effect on cell growth and morphology, while 2-deoxyribitol, in contrast, showed a dose-dependent inhibition in cell growth and increase in cell death with only about 10% of cells survive at the dose of 10 mM or higher when compared to the control (no drug treatment) as well as to the ribitol treated cells. Anchorage independent growth of the cancer cells as analyzed by formation of tumor colonies within agar gel was also found to be significantly inhibited (FIG. 3). This effect was also clearly demonstrated in the MDA231 cells (triple negative breast cancer cell) with concentrations at lower than 10 mM.

Figure 4:
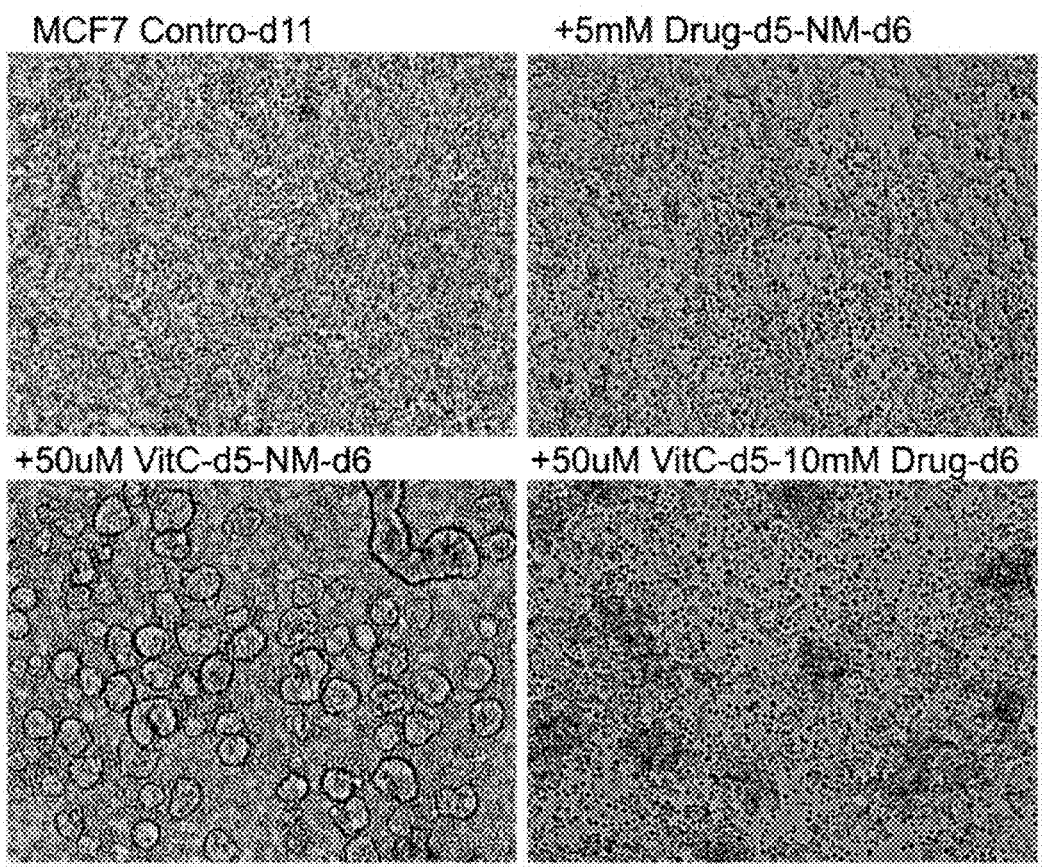
FIG. 4 shows microscopy images of MCF7 cells grown for 11 days (d11) without (control, upper left panel), or with 2-deoxyribitol (5 mM Drug, upper right panel). Cells were also treated with Vitamin C (VitC) at a concentration of 50 μM for 5 days (5d) and then returned to normal medium (NM) for 6 days (d6), without (lower left panel) or with 2-deoxyribitol (Drug, lower right panel). The formation of cancer mammospheres, considered to be cancer stem cell-rich population, can be seen in culture without Drug treatment, and with Vitamin C treatment only. Drug treatment greatly reduces to eliminates the formation of cancer mammospheres.

Importantly, as shown in FIG. 4, 2-deoxyribitol was seen to inhibit the formation of mammospheres, considered to be rich of cancer stem cells (CSC) and related to resistance to several types of chemotherapy drugs. To examine mammosphere formation, MCF7 cells were grown for 11 days with or without 2-deoxyribitol (drug) treatment (FIG. 4, top panels). In addition, MCF7 cells were treated with Vitamin C at the concentration of 50 µM for 5 days and then returned to normal medium ("NM") for 6 days (FIG. 4, lower panels). A few small and not well defined mammospheres were detected in the control, but no spheres were seen in the 5 mM drug treated cells. Replacing Vitamin C treatment with normal medium greatly increased the number of well-defined mammospheres (FIG. 4, lower left panel). The number of mammospheres decreased dramatically in the Vitamin C treated cells after further 6 day treatment with 2-deoxyribitol (FIG. 4, lower right panel).

Figure 5:
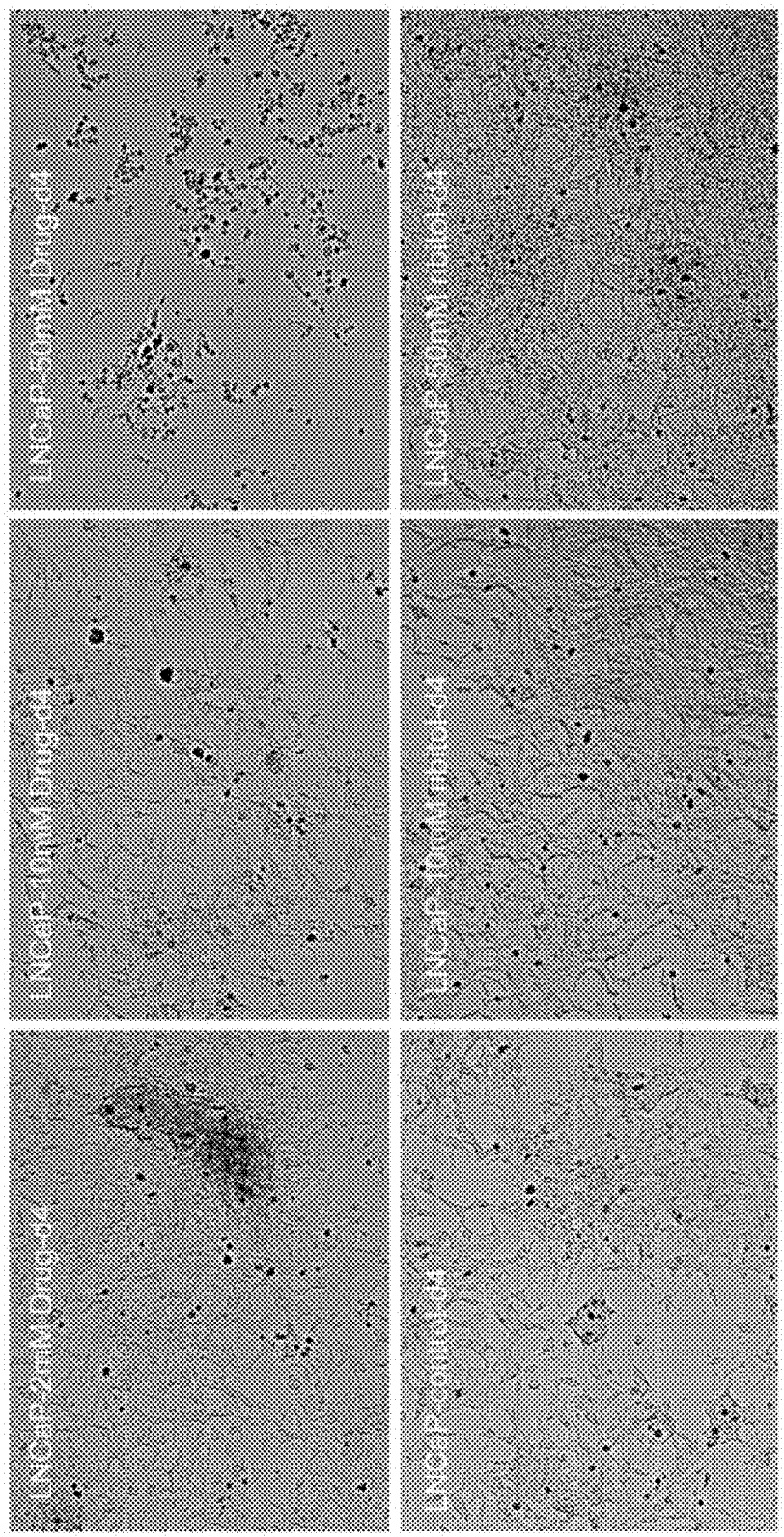
FIG. 5 shows microscopy images of the prostate cancer cell line LNCaP treated with 2-deoxyribitol (Drug) at the doses of 2 mM, 10 mM and 50 mM concentration for 4 days in comparison with untreated (control), and 10 mM and 50 mM ribitol treated cells. A dose dependent decrease in cell density was clearly detected with 2-deoxyribitol treatment, but not with ribitol treatment.

2-deoxyribitol also had an effect on inhibiting cell growth of the breast cancer T47D cells and MDA231 cells, as well as prostate cancer cells LNCaP. Similarly, a dose dependent inhibition in cell growth and death was demonstrated in the LNCaP prostate cancer cells, as shown in FIG. 5. Less than 50% of cells and 10% of cells were detected with the treatment of 10 mM and 50 mM 2-deoxyribitol, respectively. Most remaining cells at the higher dosage had reduced cellular size and a rounded shape with nuclear fragmentation, suggesting an apoptotic death. In contrast, cell density was slightly increased with ribitol treatment.

Figure 6:
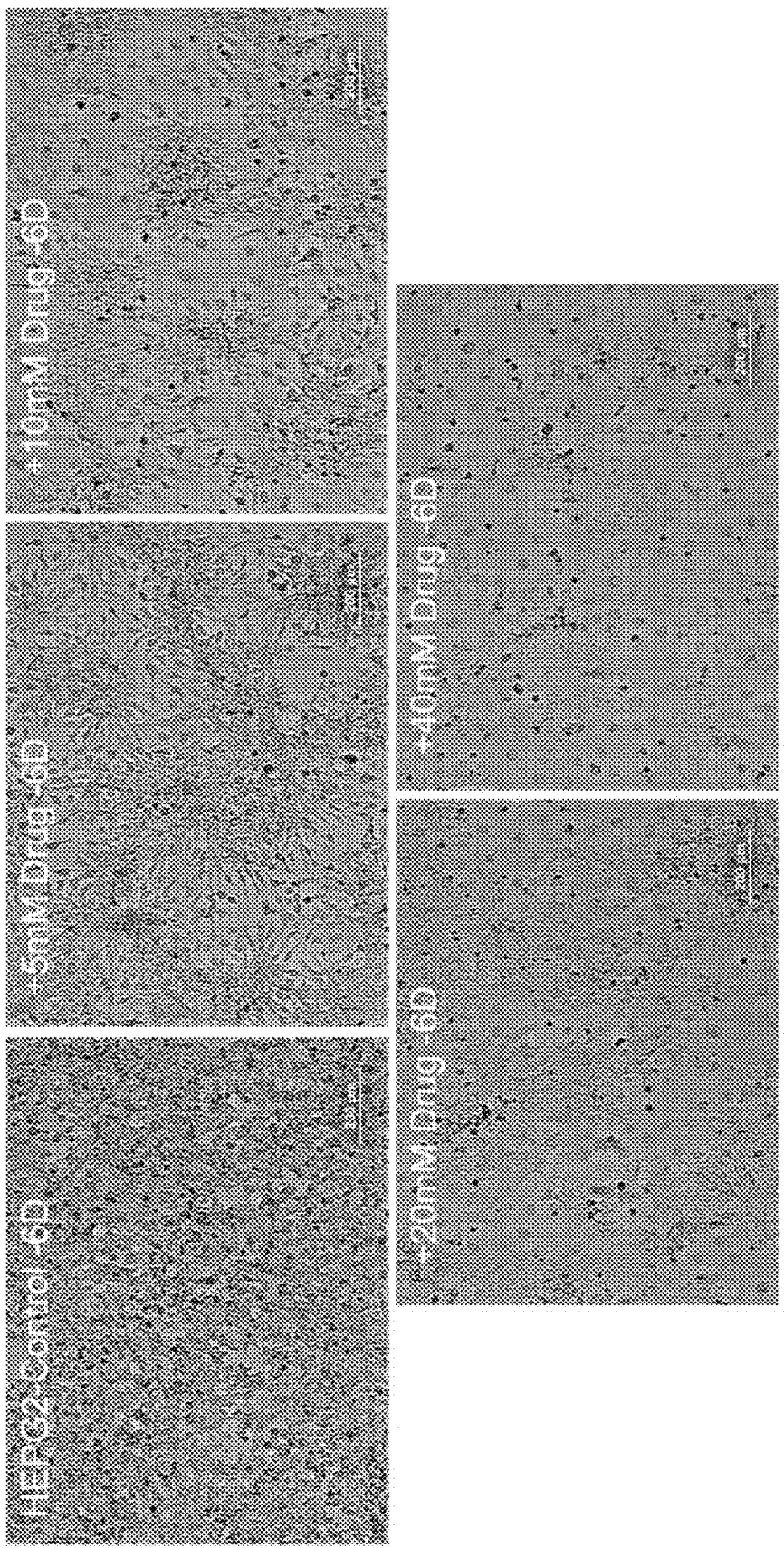
FIG. 6 shows microscopy images of hepatocarcinoma HEPG2 cells with a clonal growth pattern with tightly-packed cells filling the surrounding empty space. The cells grow into large sheets (Control; top left panel), but remain tightly packed with limited cytoplasm. Cells were treated with 5 mM (top middle panel), 10 mM (top right panel), 20 mM (bottom left panel), or 40 mM (bottom right panel) 2-deoxyribitol (Drug). A dose-dependent decrease in cell density and increase in volume of cytoplasm is observed with the drug treatment.

2-deoxyribitol was also found to be effective at inhibiting the growth of and inducing cell death in the hepatocarcinoma cell HEPG2. FIG. 6 shows a dose-dependency in cell growth inhibition and in cell death. HEPG2 cells have a clonal growth pattern with tightly-packed cells growing out to fill the surrounding empty space. The cells grow into large sheet (as visible in the top left panel of FIG. 6), but remain packed tightly with limited cytoplasm, 2-deoxyribitol treatment however decreased the number of cells with increasing amount of cytoplasm dose-dependently. The majority of the cells became three or more times larger (with abundance of cytoplasm) than the size of control cells and arranged similarly to the appearance of normal hepatocytes in liver at the dose of 20 mM or higher 2-deoxyribitol. Small numbers of cell death were also detected in the remaining narrow areas where the size of the cells was relatively smaller than those of surrounding cells.

Figure 7:
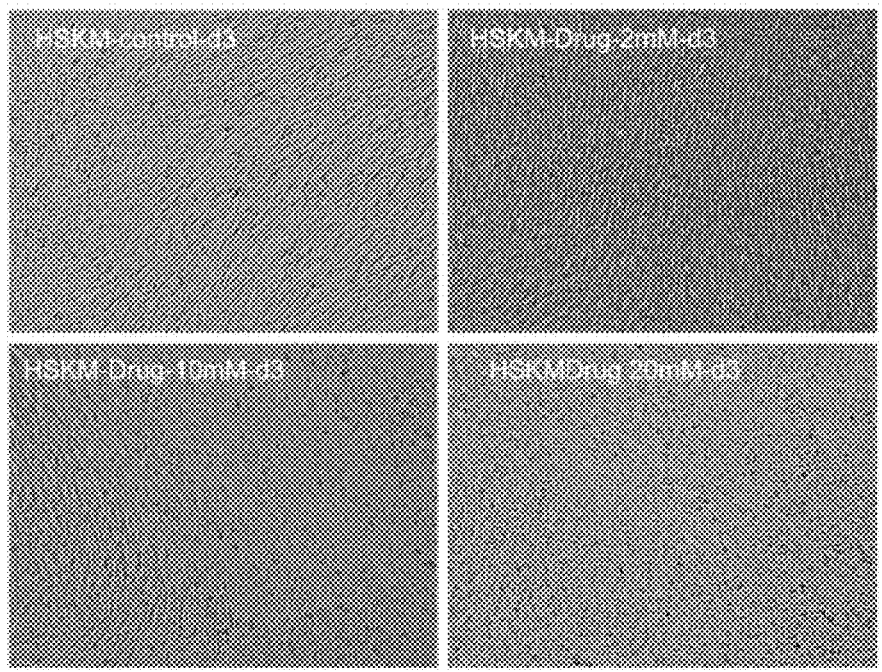
FIG. 7 shows microscopy images of normal human myoblasts (HSKM cells) treated with 2-deoxyribitol (Drug) for 3 days (d3). Three different doses were tested as labeled in the images: 2 mM (top right panel), 10 mM (bottom left panel), and 20 mM (bottom right panel) 2-deoxyribitol. No-drug control is shown in top left panel. Drug effect on growth of the cells is not clearly visible.
Figure 8:
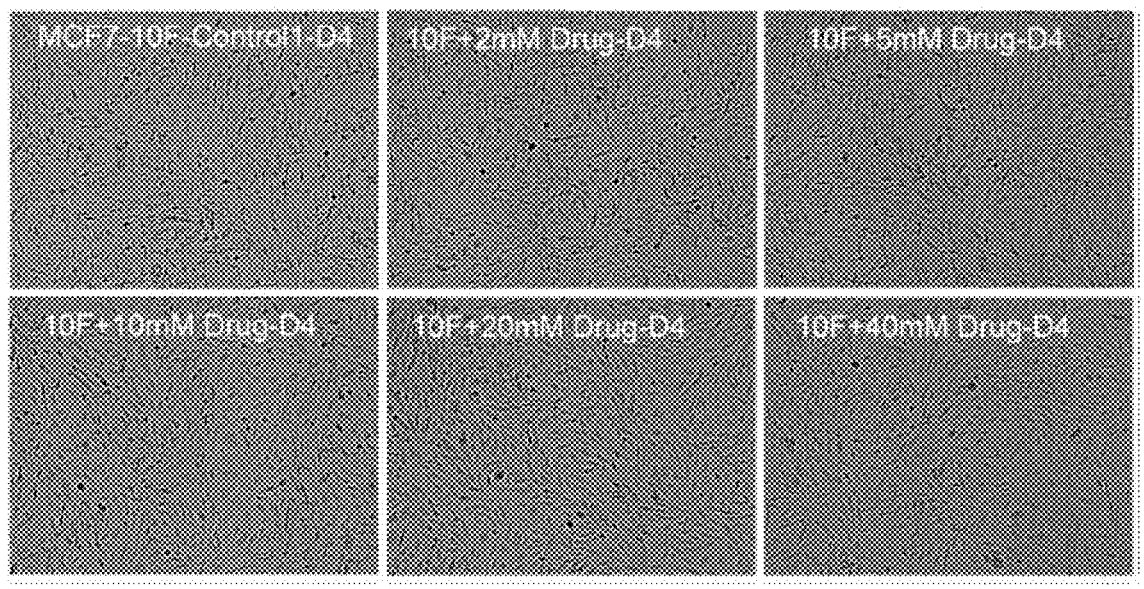
FIG. 8 shows microscopy images of normal human breast epithelial cells MCF7-10F treated with 2-deoxyribitol (Drug) for 4 days (D4). Control shows untreated cells (top left panel). 2-deoxyribitol was given in ascending doses of 2 mM (top middle panel), 5 mM (top right panel), 10 mM (bottom left panel), 20 mM (bottom middle panel), and 40 mM (bottom right panel). No significant differences were observed between the control and drug-treated cells at any dose.

In contrast, 2-deoxyribitol produced unnoticeable changes in cell culture of normal human myoblasts or differentiated myotubes (FIG. 7), indicating its low toxicity potential to normal cell populations. In this study, normal human myoblasts (HSKM cells) were treated with 2-deoxyribitol (Drug) for 3 days. No difference in cell density or myofiber formation was observed between control and drug-treated cells at three different doses. Similarly, treatment of 2-deoxyribitol also did not inhibit growth or cause cell death of normal breast cells at any dose, as modeled with breast epithelial cell MCF7-10F (FIG. 8).

2-deoxyribitol is water soluble and highly stable for at least 6 months in 4 degrees Celsius, so 2-deoxyribitol can be dissolved in water-based solution for use, 2-deoxyribitol can be formulated with excipient or other drugs and delivered together. It can be delivered by direct application to local areas, given orally or through vasculature system. 2-deoxyribitol can also be delivered before, at the same time, or after the use of other drugs. 2-deoxyribitol can be applied as treatment for cancers before, at the same time, or after any other treatment procedure(s). In addition, the effect of 2-deoxyribitol on three tissue types of cancers indicate that it can be applied for many other epithelial cancers.

In summary, 2-deoxyribitol did not enhance glycosylation of α-DG, but did exhibit unique anticancer properties. All other tested sugars including ribitol and 2-deoxyribose did not show the same anticancer effects (FIG. 10), although some of the tested compounds, including ribose, ribulose, and ribitol-5-phosphate showed an effect of enhancing glycosylation of α-DG (Pei Lu et al., (2020) Sci Rep 10(1): 4935; incorporated herein by reference in its entirety).

Also provided herein is Table 3, which shows the $IC_{50}$ determination in different types of cancer cells with 2-deoxyribitol treatment. In brief, the cells were cultures in relevant medium and treated with a range of 9 doses of 2-deoxyribitol, from 10 mM, 5 mM, 2.5 mM, 1.25 mM, 0.62 mM, 0.31 mM, 0.08 mM, and 0.04 mM. Cells were diluted in the corresponding ATCC recommended medium and dispensed in a 384-well plate, depending on the cell line used, at a density of 100-6400 cells per well in 45 µl medium. For each used cell line the optimal cell density was used. The margins of the plate were filled with phosphate-buffered saline. Plated cells were incubated in a humidified atmosphere of 5% $CO_2$ at 37° C. After 24 hours, 5 µl of compound dilution was added and plates were further incubated. At the end of experiment (t=end), 24 µl of ATPlite 1Step™ (PerkinElmer) solution was added to each well, and subsequently shaken for 2 minutes. After 10 minutes of incubation in the dark, the luminescence was recorded on an Envision multimode reader (PerkinElmer). $IC_{50}$ was determined in comparison with the control samples. The cell lines tested and their corresponding disease model is indicated the left-most and middle columns, respectively. $IC_{50}$ values are given in µM values in the right-most column. This screening was performed of a list of cancer cells to establish $IC_{50}$ values for each of the cancer cell lines. This screening provides evidence for the potential of 2DR to treat many cancer types.

TABLE 1

| Antibody | Antigen | Disease Indications |
|---|---|---|
| cetuximab | EGFR | head and neck cancer; colon cancer; colorectal cancer; non-small cell lung cancer cervical cancer, glioblastoma, renal cell cancer, ovarian epithelial, fallopian tube or primary peritoneal cancer |
| trastuzumab | HER2 | breast cancer; stomach cancer; adenocarcinoma |
| panitumumab | EGFR | colon cancer; colorectal carcinoma |
| bevacizumab | VEGF | colon cancer, ovarian cancer; lung cancer; renal cell carcinoma; glioblastoma multiforme, fallopian tube cancer, primary peritoneal cancer; cervical cancer; colorectal cancer |
| ofatumumab | CD20 | CLL/lymphoma |
| alemtuzumab | CD52 | CLL/lymphoma |
| rituximab | CD20 | leukemia (AML, ANLL, ALL), lymphoma, follicular lymphoma, diffuse large B cell lymphoma, CLL; non-Hodgkin's lymphoma |
| daratumumab | CD38 | multiple myeloma |
| SAR650984 | CD38 | multiple myeloma |
| MOR202 | CD38 | multiple myeloma |
| atezolizumab | PD-L1 | urothelial carcinoma; metastatic non-small cell lung cancer; urothelial carcinoma |
| avelumab | PD-L1 | metastatic Merkel cell carcinoma; urothelial carcinoma |
| blinatumomab | CD19/CD3 bispecific | precursor B-cell acute lymphoblastic leukemia; ALL; R/R ALL |
| dinutuximab | GD2 | neuroblastoma |
| durvalumab | PD-L1 | urothelial carcinoma; non-small cell lung cancer |
| denosumab | RANKL | bone metastases; multiple myeloma; giant cell tumor of bone; prostate cancer or breast cancer in patients receiving androgen deprivation or adjuvant aromatase inhibitor therapy (ADT or AI) |
| elotuzumab | SLAMF7 | multiple myeloma |
| ipilimumab | CTLA4 | metastatic melanoma; melanoma; renal cell carcinoma; metastatic colorectal cancer (MSI-H or dMMR, with nivolumab) |
| necitumumab | EGFR | metastatic squamous non-small cell lung carcinoma |
| nivolumab | PD-1 | melanoma; metastatic melanoma; metastatic squamous non-small cell lung cancer; renal cell carcinoma; metastatic small cell lung cancer; metastatic colorectal cancer (MSI-H or dMMR); hepatocellular carcinoma; urothelial carcinoma; SCCHM (squamous cell carcinoma of the head and neck); Hodgkin's lymphoma |
| obinutuzumab | CD20 | CLL; diffuse large B-cell lymphoma (DLBCL); NHL; follicular lymphoma (FL) |
| ocrelizumab | CD20 | multiple sclerosis |
| olaratumab | PDGFRA | soft tissue sarcoma |
| pembrolizumab | PD-1 | melanoma; non-small cell lung cancer; cervical cancer; hepatocellular carcinoma; urothelial cancer; primary mediastinal B-cell lymphoma (PMBCL); PDII + metastatic, gastric, or gastroesophageal junction adenocarcinoma; |

TABLE 1-continued

| Antibody | Antigen | Disease Indications |
|---|---|---|
| ramucirumab | VEGFR2 | Hodgkin's lymphoma; HNSCC (head and neck squamous cell carcinoma) gastric cancer; colorectal cancer; NSCLC; GEJ adenocarcinoma (gastric or gastroesophageal junction) |
| ranibizumab | VEGFR1/2 | macular degeneration |
| istiratumab | IGFR1/HER3 (ErbB3) bispecific | pancreatic cancer |
| lilotomab | CD37 | non-Hodgkin's lymphoma |
| moxetumomab | CD22 | refractory hairy cell leukemia (HCL) and acute lymphoblastic leukemia (ALL) |
| pemtumomab | MUC1 | ovarian cancer, peritoneal cancer |
| 3F8 | GD2 | neuroblastoma |
| tositumomab | CD20 | non-Hodgkin's lymphoma |
| racotumomab | NGNA ganglioside | non-small cell lung cancer |
| bemarituzumab | FGFR2 | gastroesophageal adenocarcinoma |
| cirmtuzumab | ROR1 | CLL |
| oportuzumab | EpCAM | bladder cancer |
| pertuzumab | HER2 | breast cancer |
| polatuzumab | CD79b | non-Hodskin's lymphoma; large B-cell lymphoma |
| rovalpituzumab | DLL3 | small-cell lung cancer |
| sacituzumab | Trop-2 | small cell lung cancer, pancreatic cancer, breast cancer |
| pankomab | TA-MUC1 | ovarian cancer |
| catumaxomab | CD3/EpCAM bispecific | cancer-related malignant ascites |
| duligotuzumab | HER3/EGFR (HER1) bispecific | solid tumors |
| brentuximab | CD30 | anaplastic large cell lymphoma, T cell lymphomas; Hodgkin lymphoma |
| cemiplimab-rwlc | PD-1 | cutaneous squamous cell carcinoma |
| mogamulizumab-kpkc | CCR4 | Sezary syndrome, mycosis fungoides, T cell lymphoma, |
| gemtuzumab | CD33 | CD33+ AML |
| inotuzumab | CD22 | ALL |
| bevacizumab-awwb/mvasi | VEGF | colon cancer, ovarian cancer; lung cancer; renal cell carcinoma; glioblastoma multiforme, fallopian tube cancer, primary peritoneal cancer; cervical cancer; colorectal cancer |
| CT-P10/rituximab-abbs/truxima | CD20 | leukemia (AML, ANLL, ALL), lymphoma, follicular lymphoma, diffuse large B cell lymphoma, CLL; non-Hodgkin's lymphoma |
| trastuzumab-dkst/ogivri | HER2 | breast cancer; stomach cancer; adenocarcinoma |
| trastuzumab-dttb/ontruzant | HER2 | breast cancer; stomach cancer; adenocarcinoma |
| trastuzumab-pkrb/herzuma | HER2 | breast cancer; stomach cancer; adenocarcinoma |
| GP2013/rixathon | CD20 | leukemia (AML, ANLL, ALL), lymphoma, follicular lymphoma, diffuse large B cell lymphoma, CLL; non-Hodgkin's lymphoma |
| ibritumomab | CD20 | non-Hodgkin's lymphoma |
| lifastuzumab | SLC34A2 | ovarian cancer |

TABLE 2

Cancer therapeutic agents.

| Drug | Target(s) |
|---|---|
| Abitrexate (Methotrexate) | Acute lymphoblastic leukemia; breast cancer; gestational trophoblastic disease, head and neck cancer; lung cancer; mycosis fungoides; non-Hodgkin lymphoma osteosarcoma |
| ABRAXANE ® (Paclitaxel Albumin-stabilized Nanoparticle Formulation) | Breast cancer; non-small cell lung cancer; pancreatic cancer |
| ABVD (Adriamycin, bleomycin, vinblastine sulfate, dacarbazine) | Hodgkin lymphoma |
| ABVE (Adriamycin, bleomycin, vincristine sulfate, etoposide) | Hodgkin lymphoma |
| ABVE-PC(Adriamycin, bleomycin, vincristine sulfate, etoposide, prednisone, cyclophosphamide) | Hodgkin lymphoma |
| AC (Adriamycin cyclophosphamide) | Breast cancer |
| AC-T (Adriamycin, cylclophosphamide, Taxol) | Breast cancer |
| Adcetris (Brentuximab Vedotin) | Anaplastic large cell lymphoma; Hodgkin lymphoma |
| ADE (Cytarabine (Ara-C), Daunorubicin Hydrochloride, | Acute myeloid leukemia |
| Ado-Trastuzumab Emtansine | Breast cancer |
| Adriamycin (Doxorubicin Hydrochloride) | Acute lymphoblastic leukemia; acute myeloid leukemia; breast cancer, gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor |
| Adrucil (Fluorouracil) | Basal cell carcinoma; breast cancer; colorectal cancer; gastric (stomach) adenocarcinoma; pancreatic cancer; squamous cell carcinoma of the head and neck |
| Afatinib Dimaleate | Non-small cell lung cancer |
| Afinitor (Everolimus) | Breast cancer, pancreatic cancer; renal cell carcinoma; subependymal giant cell astrocytoma |
| Alimta (Pemetrexed Disodium) | Malignant pleural mesothelioma; non-small cell lung cancer |
| Ambochlorin (Chlorambucil) | Chronic lymphocytic leukemia; Hodgkin lymphoma; non-Hodgkin |
| Anastrozole | Breast cancer |
| Aredia (Pamidronate Disodium) | Breast cancer; multiple myeloma |
| Arimidex (Anastrozole) | Breast cancer |
| Aromasin (Exemestane) | Advanced breast cancer; early-stage breast cancer and estrogen receptor |
| Arranon (Nelarabine) | T-cell acute lymphoblastic leukemia: T-cell lymphoblastic lymphoma |
| Azacitidine | Myelodysplastic syndromes |
| BEACOPP | Hodgkin lymphoma |
| Becenum (Carmustine) | Brain tumors; Hodgkin lymphoma; multiple myeloma; non-Hodgkin |
| Beleodaq (Belinostat) | Peripheral T-cell lymphoma |
| BEP | Ovarian germ cell tumors; testicular germ cell tumors |
| Bicalutamide | Prostate cancer |
| BiCNU (Carmustine) | Brain tumors; Hodgkin lymphoma; multiple myeloma; non-Hodgkin |

TABLE 2-continued

Cancer therapeutic agents.

| Drug | Target(s) |
|---|---|
| Bleomycin | Hodgkin lymphoma; non-Hodgkin lymphoma; penile cancer; squamous cell carcinoma of the cervix; squamous cell carcinoma of the head and neck; squamous cell carcinoma of the vulva; testicular cancer |
| Bosulif (Bosutinib) | Chronic myelogenous leukemia |
| Brentuximab Vedotin | Anaplastic large cell lymphoma; Hodgkin lymphoma |
| Busulfan | Chronic myelogenous leukemia |
| Busulfex (Busulfan) | Chronic myelogenous leukemia |
| Cabozantinib-S-Malate | Medullary thyroid cancer |
| CAF | Breast cancer |
| Camptosar (Irinotecan Hydrochloride) | Colorectal cancer |
| CAPOX | Colorectal cancer |
| Carfilzomib | Multiple myeloma |
| Casodex (Bicalutamide) | Prostate cancer |
| CeeNU (Lomustine) | Brain tumors; Hodgkin lymphoma |
| Ceritinib | Non-small cell lung cancer |
| Cerubidine (Daunorubicin Hydrochloride) | Acute lymphoblastic leukemia; acute leukemia |
| Chlorambucil | Chronic lymphocytic leukemia; Hodgkin lymphoma; non-Hodgkin |
| CHLORAMBUCIL-PREDNISONE | Chronic lymphocytic leukemia |
| CHOP | Non-Hodgkin lymphoma |
| Cisplatin | Bladder cancer; cervical cancer; malignant mesothelioma; non-small cell lung cancer; ovarian cancer; squamous cell carcinoma of the head and neck; testicular cancer |
| Clafen (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma |
| Clofarex (Clofarabine) | Acute lymphoblastic leukemia |
| CMF | Breast cancer |
| Cometriq (Cabozantinib-S-Malate) | Medullary thyroid cancer |
| COPP | Hodgkin lymphoma; non-Hodgkin |
| COPP-ABV | Hodgkin lymphoma |
| Cosmegen (Dactinomycin) | Ewing sarcoma; gestational trophoblastic disease; rhabdomyosarcoma; solid tumors; testicular cancer; Wilms tumor |
| CVP | Non-Hodgkin lymphoma; chronic lymphocytic leukemia |
| Cyclophosphamide | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma. |
| Cyfos (Ifosfamide) | Testicular germ cell tumors |
| Cyramza (Ramucirumab) | Adenocarcinoma; colorectal cancer; non-small cell lung cancer |
| Cytarabine | Acute lymphoblastic leukemia; acute myeloid leukemia; chronic myelogenous leukemia; meningeal leukemia |
| Cytosar-U (Cytarabine) | Acute lymphoblastic leukemia; acute myeloid leukemia; chronic myelogenous leukemia; meningeal leukemia |

TABLE 2-continued

Cancer therapeutic agents.

| Drug | Target(s) |
|---|---|
| Cytoxan (Cyclophosphamide) | Acute lymphoblastic leukemia; acute myeloid leukemia; breast cancer; chronic lymphocytic leukemia; chronic Hodgkin lymphoma; multiple myeloma; mycosis fungoides; neuroblastoma; non-Hodgkin lymphoma; ovarian cancer; retinoblastoma |
| Dacarbazine | Hodgkin lymphoma; melanoma |
| Dacogen (Decitabine) | Myelodysplastic syndromes |
| Dactinomycin | Ewing sarcoma; gestational trophoblastic disease; rhabdomyosarcoma; solid tumors; testicular cancer; Wilms tumor |
| Daunorubicin Hydrochloride | Acute lymphoblastic leukemia; acute myeloid leukemia |
| Degarelix | Prostate cancer |
| Denileukin Diftitox | Cutaneous T-cell lymphoma |
| DepoCyt (Liposomal Cytarabine) | Lymphomatous meningitis |
| DepoFoam (Liposomal Cytarabine) | Lymphomatous meningitis |
| Docetaxel | Breast cancer; adenocarcinoma of the |
| Doxil (Doxorubicin Hydrochloride Liposome) | AIDS-related Kaposi sarcoma; multiple myeloma; ovarian cancer |
| Doxorubicin Hydrochloride | Acute lymphoblastic leukemia; acute myeloid leukemia; breast |
| Dox-SL (Doxorubicin Hydrochloride Liposome) | AIDS-related Kaposi sarcoma; multiple myeloma; ovarian cancer |
| DTIC-Dome (Dacarbazine) | Hodgkin lymphoma; melanoma |
| Efudex (Fluorouracil) | Basal cell carcinoma; breast cancer; |
| Ellence (Epirubicin Hydrochloride) | Breast cancer |
| Eloxatin (Oxaliplatin) | Colorectal cancer; stage III colon cancer |
| Emend (Aprepitant) | Nausea and vomiting caused by |
| Enzalutamide | Prostate cancer |
| Epirubicin Hydrochloride | Breast cancer |
| EPOCH | Non-Hodgkin lymphoma |
| Eribulin Mesylate | Breast cancer |
| Erivedge (Vismodegib) | Basal cell carcinoma |
| Erlotinib Hydrochloride | Non-small cell lung cancer; pancreatic |
| Erwinaze (Asparaginase Erwinia | Acute lymphoblastic leukemia |
| Etopophos (Etoposide Phosphate) | Small cell lung cancer; testicular cancer |
| Evacet (Doxorubicin Hydrochloride | AIDS-related Kaposi sarcoma; multiple |
| Everolimus | Breast cancer; pancreatic cancer; renal cell carcinoma; subependymal giant cell |
| Evista (Raloxifene Hydrochloride) | Breast cancer |
| Exemestane | Breast cancer |
| Fareston (Toremifene) | Breast cancer |
| Farydak (Panobinostat) | Multiple myeloma |
| Faslodex (Fulvestrant) | Breast cancer |
| FEC | Breast cancer |
| Femara (Letrozole) | Breast cancer |
| Filgrastim | Neutropenia |
| Fludara (Fludarabine Phosphate) | Chronic lymphocytic leukemia |
| Fluoroplex (Fluorouracil) | Basal cell carcinoma; breast cancer; |
| Folex (Methotrexate) | Acute lymphoblastic leukemia; breast |
| FOLFIRI | Colorectal cancer |
| FOLFIRI-BEVACIZUMAB | Colorectal cancer |
| FOLFIRI-CETUXIMAB | Colorectal cancer |
| FOLFIRINOX | Pancreatic cancer |
| FOLFOX | Colorectal cancer |
| Folotyn (Pralatrexate) | Peripheral T-cell lymphoma |
| FU-LV | Colorectal cancer; esophageal cancer; gastric |
| Fulvestrant | Breast cancer |
| Gefitinib | Non-small cell lung cancer |

TABLE 2-continued

Cancer therapeutic agents.

| Drug | Target(s) |
|---|---|
| Gemcitabine Hydrochloride | Breast cancer; non-small cell lung cancer; ovarian cancer; pancreatic cancer |
| GEMCITABINE-CISPLATIN | Biliary tract cancer; bladder cancer; cervical |
| GEMCITABINE-OXALIPLATIN | Pancreatic cancer |
| Gemtuzumab Ozogamicin (antibody drug conjugate) | Acute myeloid leukemia |
| Gemzar (Gemcitabine Hydrochloride) | Breast cancer; non-small cell lung cancer; ovarian cancer; pancreatic cancer |
| Gilotrif (Afatinib Dimaleate) | Non-small cell lung cancer |
| Gleevec (Imatinib Mesylate) | Acute lymphoblastic leukemia; chronic eosinophilic leukemia or hypereosinophilic |
| Gliadel (Carmustine Implant) | Glioblastoma multiforme; malignant glioma |
| Goserelin Acetate | Breast cancer; prostate cancer |
| Halaven (Eribulin Mesylate) | Breast cancer |
| Hycamtin (Topotecan Hydrochloride) | Cervical cancer; ovarian cancer; small cell |
| Hyper-CVAD | Acute lymphoblastic leukemia; non-Hodgkin |
| Ibrance (Palbociclib) | Breast cancer |
| Ibrutinib | Chronic lymphocytic leukemia; mantel cell lymphoma; |
| ICE | Hodgkin lymphoma; non-Hodgkin lymphoma |
| Iclusig (Ponatinib Hydrochloride) | Acute lymphoblastic leukemia; Chronic |
| Idamycin (Idarubicin Hydrochloride) | Acute myeloid leukemia |
| Imatinib Mesylate | Acute lymphoblastic leukemia; chronic |
| Imbruvica (Ibrutinib) | Chronic lymphocytic leukemia; mantle cell lymphoma; |
| Inlyta (Axitinib) | Renal cell carcinoma |
| Iressa (Gefitinib) | Non-small cell lung cancer |
| Irinotecan Hydrochloride | Colorectal cancer |
| Istodax (Romidepsin) | Cutaneous T-cell lymphoma |
| Ixempra (Ixabepilone) | Breast cancer |
| Jevtana (Cabazitaxel) | Prostate cancer |
| Keoxifene (Raloxifene Hydrochloride) | Breast cancer |
| Kyprolis (Carfilzomib) | Multiple myeloma |
| Lenvima (Lenvatinib Mesylate) | Thyroid cancer |
| Letrozole | Breast cancer |
| Leucovorin Calcium | Colorectal cancer |
| Leukeran (Chlorambucil) | Chronic lymphocytic leukemia; Hodgkin |
| Leuprolide Acetate | Prostate cancer |
| Linfolizin (Chlorambucil) | Chronic lymphocytic leukemia; Hodgkin |
| LipoDox (Doxorubicin Hydrochloride Liposome) | AIDS-related Kaposi sarcoma; multiple myeloma; ovarian cancer |
| Lomustine | Brain tumors; Hodgkin lymphoma |
| Lupron (Leuprolide Acetate) | Prostate cancer |
| Lynparza (Olaparib) | Ovarian cancer |
| Marqibo (Vincristine Sulfate Liposome) | Acute lymphoblastic leukemia |
| Matulane (Procarbazine Hydrochloride) | Hodgkin lymphoma |
| Mechlorethamine Hydrochloride | Bronchogenic carcinoma; chronic |
| Megace (Megestrol Acetate) | Breast cancer; endometrial cancer |
| Mekinist (Trametinib) | Melanoma |
| Mercaptopurine | Acute lymphoblastic leukemia |
| Mesnex (Mesna) | Hemorrhagic cystitis |
| Methazolastone (Temozolomide) | Anaplastic astrocytoma; glioblastoma |

TABLE 2-continued

Cancer therapeutic agents.

| Drug | Target(s) |
|---|---|
| Mexate (Methotrexate) | Acute lymphoblastic leukemia; breast |
| Mexate-AQ (Methotrexate) | Acute lymphoblastic leukemia; breast |
| Mitoxantrone Hydrochloride | Acute myeloid leukemia; prostate cancer |
| Mitozytrex (Mitomycin C) | Gastric (stomach) and pancreatic adenocarcinoma |
| MOPP | Hodgkin lymphoma |
| Mozobil (Plerixafor) | Multiple myeloma; non-Hodgkin lymphoma |
| Mustargen (Mechlorethamine Hydrochloride) | Bronchogenic carcinoma; chronic lymphocytic |
| Myleran (Busulfan) | Chronic myelogenous leukemia |
| Mylotarg (Gemtuzumab Ozogamicin) | Acute myeloid leukemia |
| Nanoparticle Paclitaxel (Paclitaxel Albumin-stabilized Nanoparticle Formulation) | Breast cancer; Non-small cell lung cancer; Pancreatic cancer |
| Navelbine (Vinorelbine Tartrate) | Non-small cell lung cancer |
| Nelarabine | T-cell acute lymphoblastic leukemia |
| Neosar (Cyclophosphamide) | Acute lymphoblastic leukemia; Acute myeloid leukemia; Breast cancer; |
| Nexavar (Sorafenib Tosylate) | Hepatocellular carcinoma; Renal cell |
| Nilotinib | Chronic myelogenous leukemia |
| Nolvadex (Tamoxifen Citrate) | Breast cancer |
| Odomzo (Sonidegib) | Basal cell carcinoma |
| OEPA | Hodgkin lymphoma |
| OFF | Pancreatic cancer |
| Olaparib | Ovarian cancer |
| Oncaspar (Pegaspargase) | Acute lymphoblastic leukemia |
| OPPA | Hodgkin lymphoma |
| Oxaliplatin | Colorectal cancer; Stage III colon cancer |
| Paclitaxel | AIDS-related Kaposi sarcoma; Breast |
| Paclitaxel Albumin-stabilized Nanoparticle | Breast cancer; Non-small lung cancer; |
| PAD | Multiple myeloma |
| Palbociclib | Breast cancer |
| Pamidronate Disodium | Breast cancer; Multiple myeloma |
| Panobinostat | Multiple myeloma |
| Paraplat (Carboplatin) | Non-small cell lung cancer; Ovarian cancer |
| Paraplatin (Carboplatin) | Non-small cell lung cancer; Ovarian cancer |
| Pazopanib Hydrochloride | Renal cell carcinoma; Soft tissue sarcoma |
| Pegaspargase | Acute lymphoblastic leukemia |
| Pemetrexed Disodium | Malignant pleural mesothelioma; Non-small |
| Platinol (Cisplatin) | Bladder cancer; Cervical cancer; Malignant |
| Platinal-AQ (Cisplatin) | Bladder cancer; Cervical cancer; Malignant |
| Plerixafor | Multiple myeloma; Non-Hodgkin lymphoma |
| Pomalidomide | Multiple myeloma |
| Pomalyst (Pomalidomide) | Multiple myeloma |
| Pontinib Hydrochloride | Acute lymphoblastic leukemia; Chronic myelogenous leukemia |
| Pralatrexate | Peripheral T-cell lymphoma |
| Prednisone | Acute lymphoblastic leukemia; Chronic |
| Procarbazine Hydrochloride | Hodgkin lymphoma |
| Provenge (Sipuleucel-T) | Prostate cancer |
| Purinethol (Mercaptopurine) | Acute lymphoblastic leukemia |
| Radium 223 Dichloride | Prostate cancer |
| Raloxifene Hydrochloride | Breast cancer |
| R-CHOP | Non-Hodgkin lymphoma |
| R-CVP | Non-Hodgkin lymphoma |
| Regorafenib | Colorectal cancer; Gastrointestinal stromal |
| R-EPOCH | B-cell non-Hodgkin lymphoma |
| Revlimid (Lenalidomide) | Mantle cell lymphoma; Multiple myeloma; |
| Rheumatrex (Methotrexate) | Acute lymphoblastic leukemia; Breast |
| Romidepsin | Cutaneous T-cell lymphoma |
| Rubidomycin (Daunorubicin Hydrochloride) | Acute lymphoblastic leukemia; Acute myeloid leukemia |
| Sipuleucel-T | Prostate cancer |

TABLE 2-continued

Cancer therapeutic agents.

| Drug | Target(s) |
|---|---|
| Somatuline Depot (Lanreotide Acetate) | Gastroenteropancreatic neuroendocrine tumors |
| Sonidegib | Basal cell carcinoma |
| Sorafenib Tosylate | Hepatocellular carcinoma; Renal cell |
| Sprycel (Dasatinib) | Acute lymphoblastic leukemia: Chronic myelogenous leukemia |
| STANFORD V | Hodgkin lymphoma |
| Stivarga (Regorafenib) | Colorectal cancer; Gastrointestinal stromal |
| Sunitnib Malate | Gastrointestinal stromal tumor; Pancreatic cancer; Renal cell carcinoma |
| Sutent (Sunitinib Malate) | Gastrointestinal stromal tumor; Pancreatic cancer; Renal cell |
| Synovir (Thalidomide) | Multiple myeloma |
| Synribo (Omacetaxine Mepesuccinate) | Chronic myelogenous leukemia |
| TAC | Breast cancer |
| Tafinlar (Dabrafenib) | Melanoma |
| Tamoxifen Citrate | Breast cancer |
| Tarabine PFS (Cytarabine) | Acute lymphoblastic leukemia; Acute |
| Tarceva (Erlotinib Hydrochloride) | Non-small cell lung cancer; Pancreatic |
| Targretin (Bexarotene) | Skin problems caused by cutaneous T-cell |
| Tasigna (Niltinib) | Chronic myelogenous leukemia |
| Taxol (Paclitaxel) | AIDS-related Kaposi sarcoma; Breast |
| Taxotere (Docetaxel) | Breast cancer; Adenocarcinoma; Non-small cell lung cancer; Prostate cancer; |
| Temodar (Temozolomide) | Anaplastic astrocytoma; Glioblastoma |
| Temozolomide | Anaplastic astrocytoma; Glioblastoma multiforme |
| Thiotepa | Bladder cancer; Breast cancer; Malignant |
| Toposar (Etoposide) | Small cell lung cancer; Testicular cancer |
| Topotecan Hydrochloride | Cervical cancer; Ovarian cancer; Small cell lung cancer |
| Toremifene | Breast cancer |
| Torisel (Temsirolimus) | Renal cell carcinoma |
| TPF | Squamous cell carcinoma of the head and neck; Gastric (stomach) cancer |
| Treanda (Bendamustine Hydrochloride) | B-cell non-Hodgkin lymphoma; Chronic |
| Trisenox (Arsenic Trioxide) | Acute promyelocytic leukemia |
| Tykerb (Lapatinib Ditosylate) | Breast cancer |
| Vandetabib | Medullary thyroid cancer |
| VAMP | Hodgkin lymphoma |
| VeIP | Ovarian germ cell; Testicular cancer |
| Velban (Vinblastine Sulfate) | Breast cancer; Choriocarcinoma; Hodgkin lymphoma; Kaposi Testicular cancer |
| Velcade (Bortezomib) | Multiple myeloma; Mantle cell lymphoma |
| Velsar (Vinblastine Sulfate) | Breast cancer; Choriocarcinoma; Hodgkin |
| VePesid (Etoposide) | Small cell lung cancer; Testicular cancer |
| Viadur (Leuprolide Acetate) | Prostate cancer |
| Vidaza (Azacitidine) | Myelodysplastic syndromes |
| Vincasar PFS (Vincristine Sulfate) | Acute leukemia; Hodgkin lymphoma; |
| Vincristine Sulfate Liposome | Acute lymphoblastic leukemia |
| Vinorelbine Tartrate | Non-small cell lung cancer |
| VIP | Testicular cancer |
| Visbodegib | Basal cell carcinoma |
| Voraxaze (Glucarpidase) | Toxic blood levels of the anticancer drug |
| Votrient (Pazopanib Hydrochloride) | Renal cell carcinoma; Soft tissue sarcoma |
| Wellcovorin (Leucovorin Calcium) | Colorectal cancer; Anemia |
| Xalkori (Crizotinib) | Non-small cell lung cancer |
| Xeloda (Capecitabine) | Breast cancer; Colorectal cancer |
| XELIRI | Colorectal cancer; Esophageal cancer; |
| XELOX | Colorectal cancer |
| Xofigo (Radium 223 Dichloride) | Prostate cancer |
| Xtandi (Enzalutamide) | Prostate cancer |
| Zaltrap (Ziv-Aflibercept) | Colorectal cancer |

TABLE 2-continued

Cancer therapeutic agents.

| Drug | Target(s) |
|---|---|
| Zelboraf (Vemurafenib) | Melanoma |
| Ziv-Aflibercept | Colorectal cancer |
| Zoladex (Goserelin Acetate) | Breast cancer; Prostate cancer |
| Zolinza (Vorinostat) | Cutaneous T-cell lymphoma |
| Zometa (Zoledronic Acid) | Multiple myeloma |
| Zydelig (Idelalisib) | Chronic lymphocytic leukemia; Non-Non-small cell lung cancer |
| Zykadia (Certinib) | |
| Zytiga (Abiraterone Acetate) | Prostate cancer |

TABLE 3

IC50 determination in different cancer cells with 2-deoxyribitol treatment.

| Cell line name | Disease | | IC50 (µM) |
|---|---|---|---|
| 5637 | Bladder carcinoma | | 9329 |
| 786-O | Renal cell carcinoma | | 8572 |
| A-172 | Glioblastoma | > | 10000 |
| A-204 | Embryonal rhabdomyosarcoma | | 6059 |
| A-427 | Lung adenocarcinoma | | 3949 |
| A-498 | Renal cell carcinoma | | 8727 |
| A-549 | Lung adenocarcinoma | | 9973 |
| ACHN | Papillary renal cell carcinoma | | 3144 |
| BT-549 | Invasive ductal carcinoma | | 4270 |
| BxPC-3 | Pancreatic ductal adenocarcinoma | | 7814 |
| C-33 A | Cervical squamous cell carcinoma | | 7599 |
| CCF-STTG1 | Astrocytoma | | 5839 |
| CCRF-CEM | Childhood T acute lymphoblastic leukemia | | 5970 |
| COLO 205 | Colon adenocarcinoma | | 4545 |
| COLO 829 | Cutaneous melanoma | | 6370 |
| Daoy | Medulloblastoma | | 6242 |
| DB | Diffuse large B-cell lymphoma | | 4084 |
| DLD-1 | Colon adenocarcinoma | | 4534 |
| DU 145 | Prostate carcinoma | | 4867 |
| DU4475 | Breast carcinoma | | 5719 |
| ES-2 | Ovarian clear cell adenocarcinoma | | 8742 |
| G-361 | Melanoma | > | 10000 |
| HCT-15 | Colon adenocarcinoma | | 7701 |
| HCT 116 | Colon carcinoma | | 5730 |
| HL-60 | Adult acute myeloid leukemia | | 7463 |
| HT | Diffuse large B-cell lymphoma | | 6887 |
| HT-1080 | Fibrosarcoma | | 4389 |
| HuTu 80 | Duodenal adenocarcinoma | | 4921 |
| J82 | Bladder carcinoma | | 3632 |
| JAR | Gestational choriocarcinoma | | 3601 |
| Jurkat E6.1 | Childhood T acute lymphoblastic leukemia | | 4654 |
| KU812 | Chronic myelogenous leukemia | | 4301 |
| LS 174T | Colon adenocarcinoma | | 2516 |
| LS411N | Cecum adenocarcinoma | | 6969 |
| MG-63 | Osteosarcoma | | 9271 |
| MIA PaCa-2 | Pancreatic ductal adenocarcinoma | | 4870 |
| MOLT-4 | Adult T acute lymphoblastic leukemia | | 4941 |
| NCI-H460 | Large cell lung carcinoma | | 3175 |
| NCI-H82 | Small cell lung carcinoma | | 2945 |
| PA-1 | Ovarian mixed germ cell tumor | | 3488 |
| PC-3 | Prostate carcinoma | | 3679 |
| RKO | Colon carcinoma | | 5775 |
| RL | Diffuse large B-cell lymphoma | | 3395 |
| RL95-2 | Endometrial adenosquamous carcinoma | | 6415 |
| RPMI-7951 | Melanoma | | 6767 |
| RS4-11 | Adult B acute lymphoblastic leukemia | | 3063 |
| RT4 | Bladder carcinoma | > | 10000 |
| SJCRH30 | Alveolar rhabdomyosarcoma | | 4461 |
| SR | Anaplastic large cell lymphoma | | 4248 |
| SU-DHL-1 | Anaplastic large cell lymphoma | | 2650 |
| SU-DHL-6 | Diffuse large B-cell lymphoma | | 4064 |
| SUP-T1 | Childhood T lymphoblastic lymphoma | | 3063 |
| SW48 | Colon adenocarcinoma | | 4489 |
| SW620 | Colon adenocarcinoma | | 5220 |
| SW837 | Rectal adenocarcinoma | | 9792 |
| SW900 | Squamous cell lung carcinoma | | 3187 |
| SW948 | Colon adenocarcinoma | | 2526 |
| SW982 | Biphasic synovial sarcoma | | 2783 |
| T24 | Bladder carcinoma | > | 10000 |
| THP-1 | Childhood acute monocytic leukemia | | 5190 |
| VA-ES-BJ | Epithelioid sarcoma | | 5282 |

The foregoing is illustrative of the present invention, and is not to be construed as limiting thereof. The invention is defined by the following claims, with equivalents of the claims to be included therein.

That which is claimed is:

1. A method of treating cancer in a subject in need thereof, comprising administering to the subject an effective amount of a composition comprising a 2-deoxyribitol, thereby treating the cancer in the subject.

2. A method of inhibiting and/or reducing metastasis of cancer cells and/or inducing cell death of cancer cells in a subject in need thereof, comprising administering to the subject an effective amount of a composition comprising 2-deoxyribitol, thereby inhibiting and/or reducing metastasis of the cancer cells in the subject.

3. The method of claim 1, wherein the administration of the 2-deoxyribitol is in combination with any other anticancer agent or anticancer treatment.

4. A method of enhancing the therapeutic efficacy of an anticancer agent or anticancer treatment in a subject having or at risk of cancer and receiving said anticancer agent or anticancer treatment, comprising administering to the subject an effective amount of a composition comprising a 2-deoxyribitol, thereby enhancing the therapeutic efficacy of the anticancer agent or anticancer treatment in the subject.

5. The method of claim 3, wherein the administration of the 2-deoxyribitol is before, after, and/or concurrent with the administration of the anticancer agent or anticancer treatment.

6. The method of claim 1, wherein the administration of the 2-deoxyribitol inhibits growth of cancer stem cells.

7. The method of claim 1, wherein the 2-deoxyribitol is administered topically, intravenously, cutaneously, subcutaneously, intraperitoneally, intra-arterially, intratumorally, intrathecally, intramuscularly, orally, intranasally, sublingually, via inhalation, in an implant, in a matrix, in a gel, or any combination thereof.

8. The method of claim 1, wherein the cancer is breast cancer, liver cancer, prostate cancer, bladder carcinoma, renal cell carcinoma, glioblastoma, rhabdomyosarcoma, lung cancer, invasive ductal carcinoma, pancreatic cancer, cervical cancer, astrocytoma, leukemia, colon cancer, melanoma, medulloblastoma, lymphoma, ovarian cancer, fibrosarcoma, duodenal adenocarcinoma, choriocarcinoma, cecum adenocarcinoma, osteosarcoma, endometrial cancer, synovial carcinoma, epithelioid sarcoma, or any combination thereof.

9. The method of claim 1, wherein the cancer is breast cancer, liver cancer, prostate cancer, or any combination thereof.

10. The method of claim 1, wherein the cancer is breast cancer.

11. The method of claim 1, wherein the 2-deoxyribitol is present in the composition at a concentration of about 5 µM to about 50 mM.

12. The method of claim 11, wherein the 2-deoxyribitol is present in the composition at a concentration of about 0.5 mM to about 10 mM.

13. The method of claim 3, wherein the anticancer agent or anticancer treatment is selected from the group consisting of Doxorubicin, cyclophosphamide, 5-flurouracil, vinorelbine, pembrolizumab, nivolumab, durvalumab, Paclitaxel, Docetaxel, Oligomycin, JQ1, emodin, metformin, shikonin, physcion (6PGD inhibitor), AICAR, oxythiamine, leflunomide, lonidamine, polydatin, honokiol, dehydropiandrosterone (DHEA), venetoclax (ABT-199, Bcl-2 inhibitor), navitoclax (ABT-263), A-1331852 (Bcl-xL inhibitor), ABT-737, S63845 (Mcl-1 inhibitor), and any combination thereof.

14. The method of claim 1, wherein the subject is a human patient.

15. The method of claim 1, wherein the composition comprising the 2-deoxyribitol further comprises a pharmaceutically acceptable carrier.

16. The method of claim 4, wherein the anticancer agent or anticancer treatment is selected from the group consisting of Doxorubicin, cyclophosphamide, 5-flurouracil, vinorelbine, pembrolizumab, nivolumab, durvalumab, Paclitaxel, Docetaxel, Oligomycin, JQ1, emodin, metformin, shikonin, physcion (6PGD inhibitor), AICAR, oxythiamine, leflunomide, lonidamine, polydatin, honokiol, dehydropiandrosterone (DHEA), venetoclax (ABT-199, Bcl-2 inhibitor), navitoclax (ABT-263), A-1331852 (Bcl-xL inhibitor), ABT-737, S63845 (Mcl-1 inhibitor), and any combination thereof.

17. The method of claim 2, wherein the subject is a human patient.

18. The method of claim 4, wherein the subject is a human patient.

19. The method of claim 2, wherein the cancer cells are cells of breast cancer, liver cancer, prostate cancer, bladder carcinoma, renal cell carcinoma, glioblastoma, rhabdomyosarcoma, lung cancer, invasive ductal carcinoma, pancreatic cancer, cervical cancer, astrocytoma, leukemia, colon cancer, melanoma, medulloblastoma, lymphoma, ovarian cancer, fibrosarcoma, duodenal adenocarcinoma, choriocarcinoma, cecum adenocarcinoma, osteosarcoma, endometrial cancer, synovial carcinoma, epithelioid sarcoma, or any combination thereof.

20. The method of claim 4, wherein the cancer is breast cancer, liver cancer, prostate cancer, bladder carcinoma, renal cell carcinoma, glioblastoma, rhabdomyosarcoma, lung cancer, invasive ductal carcinoma, pancreatic cancer, cervical cancer, astrocytoma, leukemia, colon cancer, melanoma, medulloblastoma, lymphoma, ovarian cancer, fibrosarcoma, duodenal adenocarcinoma, choriocarcinoma, cecum adenocarcinoma, osteosarcoma, endometrial cancer, synovial carcinoma, epithelioid sarcoma, or any combination thereof.

* * * * *

UNITED STATES PATENT AND TRADEMARK OFFICE
CERTIFICATE OF CORRECTION

PATENT NO. : 12,257,214 B2
APPLICATION NO. : 17/830858
DATED : March 25, 2025
INVENTOR(S) : Lu et al.

Page 1 of 1

It is certified that error appears in the above-identified patent and that said Letters Patent is hereby corrected as shown below:

In the Specification

Column 16, Line 49: correct "Bel-2" to read --Bcl-2--

Signed and Sealed this
Twelfth Day of August, 2025

Coke Morgan Stewart
*Acting Director of the United States Patent and Trademark Office*